US008506963B2

(12) United States Patent
Li et al.

(10) Patent No.: US 8,506,963 B2
(45) Date of Patent: Aug. 13, 2013

(54) ANTI-EFGRV3 MONOCLONAL ANTIBODY

(75) Inventors: Zonghai Li, Shanghai (CN); Huamao Wang, Shanghai (CN); Hua Jiang, Shanghai (CN); Bizhi Shi, Shanghai (CN); Jianren Gu, Shanghai (CN); Shengli Yang, Shanghai (CN)

(73) Assignee: Shanghai Cancer Institute, Shanghai (CN)

( * ) Notice: Subject to any disclaimer, the term of this patent is extended or adjusted under 35 U.S.C. 154(b) by 0 days.

(21) Appl. No.: 13/497,763

(22) PCT Filed: Sep. 22, 2009

(86) PCT No.: PCT/CN2009/074090
§ 371 (c)(1),
(2), (4) Date: Jun. 4, 2012

(87) PCT Pub. No.: WO2011/035465
PCT Pub. Date: Mar. 31, 2011

(65) Prior Publication Data
US 2013/0039920 A1 Feb. 14, 2013

(51) Int. Cl.
*A61K 39/395* (2006.01)
*C12P 19/34* (2006.01)

(52) U.S. Cl.
USPC .............. 424/141.1; 424/143.1; 435/91.1

(58) Field of Classification Search
None
See application file for complete search history.

(56) References Cited

FOREIGN PATENT DOCUMENTS

| CN | 101602808 | 12/2009 |
| WO | 02/092771 | 11/2002 |

OTHER PUBLICATIONS

Ullrich et al, "Human epidermal growth factor receptor cDNA sequence and aberrant expression of the amplified gene in A431 epidermoid carcinoma cells," Nature, 1984, vol. 309, pp. 418-425.
Downward et al. "Close similarity of epidermal growth factor receptor and v-erb-B oncogene protein sequences," Nature, 1984, vol. 307, pp. 521-527.
Libermann et al. "Amplification, enhanced expression and possible rearrangement of EGF receptor gene in primary human brain tumors of glial origin," Nature, 1985, vol. 313, pp. 144-147.
Wong et al. "Increased expression of the epidermal growth factor receptor gene in malignant gliomas is invariably associated with gene amplification," Proc. Natl. Acad. Sci. USA, 1987, vol. 84, pp. 6899-6903.
Yamazaki et al. "Amplification of the structurally and functionally altered epidermal growth factor receptor gene (c-erbB) in human brain tumors," Molecular and Cellular Biology, 1988, vol. 8, pp. 1816-1820.

Malden et al. "Selective amplification of the cytoplasmic domain of the epidermal growth factor receptor gene in glioblastoma multiforme," Cancer Research, 1988, vol. 48, pp. 2711-2714.
Modjtahedi et al., "The receptor for EGF and its ligands: expression, prognostic value and target for therapy in cancer," International Journal of Oncology, 1994, vol. 4, pp. 277-296.
Fung et al. "Activation of the cellular oncogene c-erbB by LTR insertion: molecular basis for induction of erythroblastosis by avian leukosis virus," Cell, 1983, vol. 33, pp. 357-368.
Yamamoto et al. "A new avian erythroblastosis virus, AEV-H carries erbB gene responsible for the induction of both erythroblastosis and sarcomas," Cell, 1983, vol. 34, pp. 225-232.
Nilsen et al. "c-erbB activation in ALV-induced erythroblastosis: novel RNA processing and promoter insertion result in expression of an amino-truncated EGF receptor," Cell, 1985, vol. 41, pp. 719-726.
Gamett et al. "Differences in sequences encoding the carboxy-terminal domain of the epidermal growth factor receptor correlate with differences in the disease potential of viral erbB genes," Proc. Natl. Acad. Sci. USA, 1986, vol. 83, pp. 6053-6057.
Gilmore et al. "Protein phosphorylation at tyrosine is induced by the v-erbB gene product in vivo and in vitro," Cell, 1985, vol. 40, pp. 609-618.
Kris et al. "Antibodies against a synthetic peptide as a probe for the kinase activity of the avian EGF receptor and v-erbB protein," Cell, 1985, vol. 40, pp. 619-625.
Raines et al. "c-erbB activation in avian leukosis virus-induced erythroblastosis: clustered integration sites and the arrangement of provirus in the c-erbB alleles," Proc. Natl. Acad, Sci, USA, 1985, vol. 82, pp. 2287-2291.
Pelley et al. "Proviral-activated c-erbB is leukemogenic but not sarcomagenic: characterization of a replication-competent retrovirus containing the activated c-erbB," Journal of Virology, 1988, vol. 62, pp. 1840-1844.
Wells et al, "Genetic determinant of neoplastic transformation by the retroviral oncogene v-erbB," Proc. Natl. Acad, Sci. USA, 1988, vol. 85, pp. 7597-7601.
Wikstrand et al. "Monoclonal antibodies against EGFRvIII are tumor specific and react with breast and lung carcinomas malignant gliomas," Cancer Research, 1995, vol. 55, pp. 3140-3148.
Olapade-Olaopa et al. "Evidence for the differential expression of a variant EGF receptor protein in human prostate cancer," Br J Cancer., 2000, vol. 82, No, 1, pp. 186-194.

(Continued)

*Primary Examiner* — Elly-Gerald Stoica
(74) *Attorney, Agent, or Firm* — Hamre, Schumann, Mueller & Larson, P.C.

(57) ABSTRACT

The invention provides specific binding proteins and the uses thereof. Particularly, the present invention provides a monoclonal antibody which can effectively bind to epidermal growth factor receptor variant type III (EGFRvIII) or can partially bind to the epidermal growth factor receptor (EGFR) over-expressed in cells, but not bind to EGFR normally-expressed in cells. Furthermore, the present invention said antibody has obvious therapeutic effect on a tumor cell line expressing the EGFRvIII. The invention also provides a method for preparing said monoclonal antibody and a pharmaceutical composition comprising said monoclonal antibody.

9 Claims, 10 Drawing Sheets

(56) References Cited

OTHER PUBLICATIONS

Ge et al. "Evidence of high incidence of EGFRvIII expression and coexpression with EGFR in human invasive breast cancer by laser capture microdissection and immunohistochemical analysis," Int J. Cancer., 2002, vol. 98, No. 3, pp. 357-361.

Moscatello et al. "Frequent expression of a mutant epidermal growth factor receptor in multiple human tumors," Cancer Res., 1995, vol. 55, pp. 5536-5539.

Garcia de Palazzo, et al. "Expression of mutated epidermal growth factor receptor by non-small cell lung carcinomas," Cancer Res., 1993, vol. 53, pp. 3217-3220.

Luo et al, "Suppression of EGFRvIII-mediated proliferation and tumorigenesis of breast cancer cells by ribozyme," Int. J. Cancer, 2003, vol. 104, pp. 716-721.

Kuan et al. "EGF mutant receptor vIII as a molecular target in cancer therapy," Endocrine-Related Cancer, 2001, vol. 8, pp. 83-96.

Scott et al, "A phase I clinical trial with monoclonal antibody ch806 targeting transitional state and mutant epidermal growth factor receptors," PNAS, 2007, vol. 104, No. 10, pp. 4071-4076.

Roark et al., "Breakdown of B cell tolerance in a mouse model of systemic lupus erythematosus," J. Exp. Med., 1995, vol. 181, pp. 1157-1167.

International Search Report of international application PCT/CN2009/074090, dated Jul. 8, 2010 (10 page).

Written Opinion of the International Searching Authority of international application PCT/CN2009/074090, dated Jul. 8, 2010 (7 pages).

```
  1 atgagagtgctgattcttttgtggctgttcacagcctttcctggtttcctgtctgatgtg
  1  M  R  V  L  I  L  L  W  L  F  T  A  F  P  G  F  L  S  D  V 61 cagcttcaggagtcgggacctggcctggtgaagccttctcagtctctgtccctcacctgc
 21  Q  L  Q  E  S  G  P  G  L  V  K  P  S  Q  S  L  S  L  T  C
                                                         CDRH1
121 actgtcactgcctactcagtcaccagtgattatgcctggaactggatccggcagtttcca
 41  T  V  T  A  Y  S  V  T  S  D  Y  A  W  N  W  I  R  Q  F  P
                                                         CDRH2
181 ggaaacaaactggagtggatgggctacataagctacagtggtaccactagatacaaccca
 61  G  N  K  L  E  W  M  G  Y  I  S  Y  S  G  T  T  R  Y  N  P 241 tctctcaaaagtcgaatctctatcactcgagacacatccaagaaccagttcttcctgcag
 81  S  L  K  S  R  I  S  I  T  R  D  T  S  K  N  Q  F  F  L  Q
                                                         CDRH3
301 ttgaattctatgactgctgaggacacagccacatattattgttcaagacagggacggggg
101  L  N  S  M  T  A  E  D  T  A  T  Y  Y  C  S  R  Q  G  R  G 361 tttccttactggggccaagggactctggtcactgtctctgcagccaaaacgacacccca
121  F  P  Y  W  G  Q  G  T  L  V  T  V  S  A  A  K  T  T  P  P 421 tctgtctatccactggcccctggatctgctgcccaaact
141  S  V  Y  P  L  A  P  G  S  A  A  Q  T   (SEQ ID NO:1 and 2)
```

Fig.13

```
  1 atggtccttgctcagtttcttgcattcttgttgctttggtttccaggtgcaagatgtgac
  1  M  V  L  A  Q  F  L  A  F  L  L  L  W  F  P  G  A  R  C  D 61 atcctgatgacccaatctccatcctccatgtctgtatctctgggagacacagtcagcatc
 21  I  L  M  T  Q  S  P  S  S  M  S  V  S  L  G  D  T  V  S  I
                                                         CDRL1
121 acttgccatgcaagtcaggacattaacagtaatataggtggttgcaacagaaaccaggg
 41  T  C  H  A  S  Q  D  I  N  S  N  I  G  W  L  Q  Q  K  P  G
                                                         CDRL2
181 aaatcatttaagggcctgatctatcatggaaccaacttggaagatggagttccatcaagg
 61  K  S  F  K  G  L  I  Y  H  G  T  N  L  E  D  G  V  P  S  R 241 ttcagtggcagtggatctggagcagattattctctcaccatcagcagcctggaatctgaa
 81  F  S  G  S  G  S  G  A  D  Y  S  L  T  I  S  S  L  E  S  E
                                                         CDRL3
301 gattttgcagactattactgtgtgcagtatgctcagtttccgtggacgttcggtggaggc
101  D  F  A  D  Y  Y  C  V  Q  Y  A  Q  F  P  W  T  F  G  G 361 accaaactggaaatcaaacggctgatgctgcaccaactgtatccatcttcccacca
121  T  K  L  E  I  K  R  A  D  A  A  P  T  V  S  I  F  P  P
        (SEQ ID NO: 3 and 4)
```

Fig.14

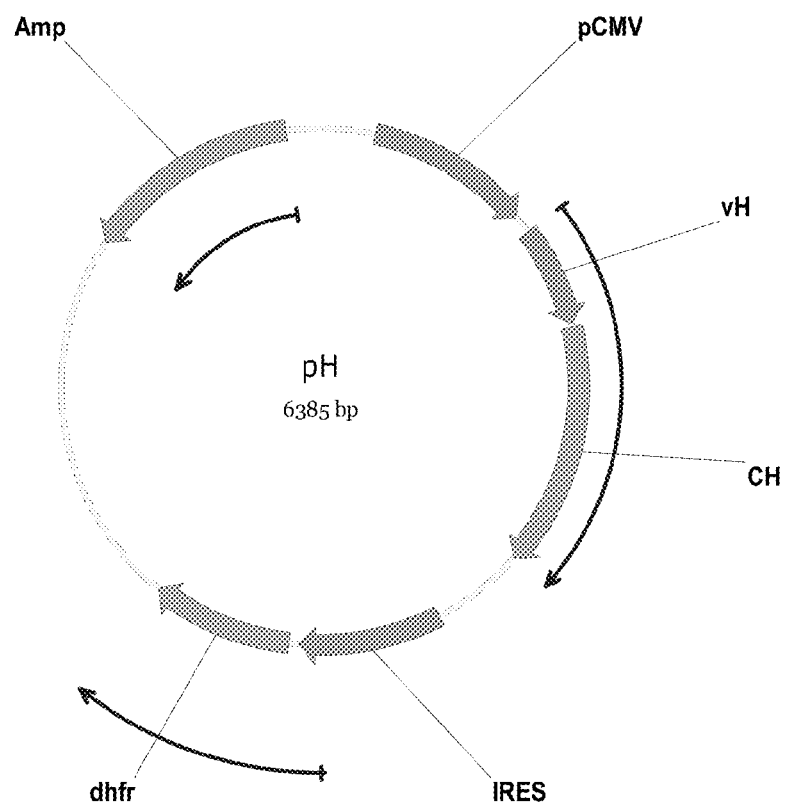
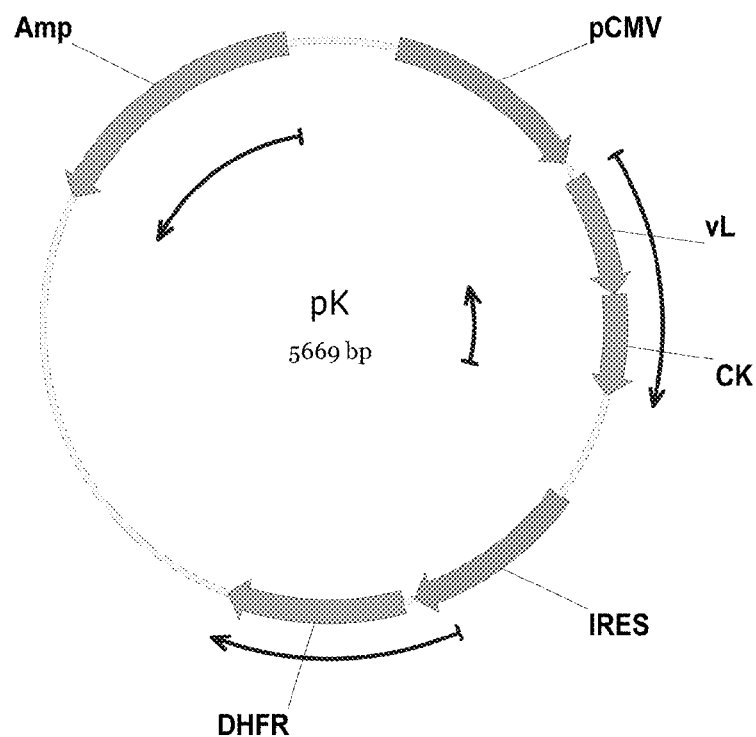
Fig.15

SEQUENCE LISTING

<160> NUMBER OF SEQ ID NOS: 17

<210> SEQ ID NO 1
<211> LENGTH: 512
<212> TYPE: DNA
<213> ORGANISM: Mus musculus
<220> FEATURE:
<222> LOCATION: (54)..(512)

<400> SEQUENCE: 1

```
tatcgctctc actggaggct gatctctgaa gataaggagg tgtagcctaa aag atg        56
                                                            Met
                                                            1 aga gtg ctg att ctt ttg tgg ctg ttc aca gcc ttt cct ggt ttc ctg      104
Arg Val Leu Ile Leu Leu Trp Leu Phe Thr Ala Phe Pro Gly Phe Leu
        5                  10                  15 tct gat gtg cag ctt cag gag tcg gga cct ggc ctg gtg aag cct tct      152
Ser Asp Val Gln Leu Gln Glu Ser Gly Pro Gly Leu Val Lys Pro Ser
             20                  25                  30 cag tct ctg tcc ctc acc tgc act gtc act gcc tac tca gtc acc agt      200
Gln Ser Leu Ser Leu Thr Cys Thr Val Thr Ala Tyr Ser Val Thr Ser
         35                  40                  45 gat tat gcc tgg aac tgg atc cgg cag ttt cca gga aac aaa ctg gag      248
Asp Tyr Ala Trp Asn Trp Ile Arg Gln Phe Pro Gly Asn Lys Leu Glu
 50                  55                  60                  65 tgg atg ggc tac ata agc tac agt ggt acc act aga tac aac cca tct      296
Trp Met Gly Tyr Ile Ser Tyr Ser Gly Thr Thr Arg Tyr Asn Pro Ser
                 70                  75                  80 ctc aaa agt cga atc tct atc act cga gac aca tcc aag aac cag ttc      344
Leu Lys Ser Arg Ile Ser Ile Thr Arg Asp Thr Ser Lys Asn Gln Phe
             85                  90                  95 ttc ctg cag ttg aat tct atg act gct gag gac aca gcc aca tat tat      392
Phe Leu Gln Leu Asn Ser Met Thr Ala Glu Asp Thr Ala Thr Tyr Tyr
        100                 105                 110 tgt tca aga cag gga cgg ggg ttt cct tac tgg ggc caa ggg act ctg      440
Cys Ser Arg Gln Gly Arg Gly Phe Pro Tyr Trp Gly Gln Gly Thr Leu
    115                 120                 125 gtc act gtc tct gca gcc aaa acg aca ccc cca tct gtc tat cca ctg      488
Val Thr Val Ser Ala Ala Lys Thr Thr Pro Pro Ser Val Tyr Pro Leu
130                 135                 140                 145 gcc cct gga tct gct gcc caa act                                      512
Ala Pro Gly Ser Ala Ala Gln Thr
                150
```

<210> SEQ ID NO 2
<211> LENGTH: 153
<212> TYPE: PRT
<213> ORGANISM: Mus musculus

<400> SEQUENCE: 2

```
Met Arg Val Leu Ile Leu Leu Trp Leu Phe Thr Ala Phe Pro Gly Phe
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Ala Tyr Ser Val Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Tyr Ser Gly Thr Thr Arg Tyr Asn Pro
65                  70                  75                  80
```

```
Ser Leu Lys Ser Arg Ile Ser Ile Thr Arg Asp Thr Ser Lys Asn Gln
            85                  90                  95

Phe Phe Leu Gln Leu Asn Ser Met Thr Ala Glu Asp Thr Ala Thr Tyr
            100                 105                 110

Tyr Cys Ser Arg Gln Gly Arg Gly Phe Pro Tyr Trp Gly Gln Gly Thr
            115                 120                 125

Leu Val Thr Val Ser Ala Ala Lys Thr Thr Pro Pro Ser Val Tyr Pro
    130                 135                 140

Leu Ala Pro Gly Ser Ala Ala Gln Thr
145                 150

<210> SEQ ID NO 3
<211> LENGTH: 451
<212> TYPE: DNA
<213> ORGANISM: Mus musculus
<220> FEATURE:
<222> LOCATION: (35)..(451)

<400> SEQUENCE: 3
attgtcttta caatcaggac tcagcatgga catg atg gtc ctt gct cag ttt ctt        55
                                     Met Val Leu Ala Gln Phe Leu
                                      1               5 gca ttc ttg ttg ctt tgg ttt cca ggt gca aga tgt gac atc ctg atg        103
Ala Phe Leu Leu Leu Trp Phe Pro Gly Ala Arg Cys Asp Ile Leu Met
         10                  15                  20 acc caa tct cca tcc tcc atg tct gta tct ctg gga gac aca gtc agc        151
Thr Gln Ser Pro Ser Ser Met Ser Val Ser Leu Gly Asp Thr Val Ser
     25                  30                  35 atc act tgc cat gca agt cag gac att aac agt aat ata ggg tgg ttg        199
Ile Thr Cys His Ala Ser Gln Asp Ile Asn Ser Asn Ile Gly Trp Leu
 40                  45                  50                  55 caa cag aaa cca ggg aaa tca ttt aag ggc ctg atc tat cat gga acc        247
Gln Gln Lys Pro Gly Lys Ser Phe Lys Gly Leu Ile Tyr His Gly Thr
                 60                  65                  70 aac ttg gaa gat gga gtt cca tca agg ttc agt ggc agt gga tct gga        295
Asn Leu Glu Asp Gly Val Pro Ser Arg Phe Ser Gly Ser Gly Ser Gly
             75                  80                  85 gca gat tat tct ctc acc atc agc agc ctg gaa tct gaa gat ttt gca        343
Ala Asp Tyr Ser Leu Thr Ile Ser Ser Leu Glu Ser Glu Asp Phe Ala
         90                  95                 100 gac tat tac tgt gtg cag tat gct cag ttt ccg tgg acg ttc ggt gga        391
Asp Tyr Tyr Cys Val Gln Tyr Ala Gln Phe Pro Trp Thr Phe Gly Gly
     105                 110                 115 ggc acc aaa ctg gaa atc aaa cgg gct gat gct gca cca act gta tcc        439
Gly Thr Lys Leu Glu Ile Lys Arg Ala Asp Ala Ala Pro Thr Val Ser
120                 125                 130                 135 atc ttc cca cca                                                         451
Ile Phe Pro Pro <210> SEQ ID NO 4
<211> LENGTH: 139
<212> TYPE: PRT
<213> ORGANISM: Mus musculus

<400> SEQUENCE: 4

Met Val Leu Ala Gln Phe Leu Ala Phe Leu Leu Leu Trp Phe Pro Gly
 1               5                  10                  15

Ala Arg Cys Asp Ile Leu Met Thr Gln Ser Pro Ser Ser Met Ser Val
             20                  25                  30

Ser Leu Gly Asp Thr Val Ser Ile Thr Cys His Ala Ser Gln Asp Ile
```

```
                    35                  40                  45
Asn Ser Asn Ile Gly Trp Leu Gln Gln Lys Pro Gly Lys Ser Phe Lys
 50                  55                  60

Gly Leu Ile Tyr His Gly Thr Asn Leu Glu Asp Gly Val Pro Ser Arg
 65                  70                  75                  80

Phe Ser Gly Ser Gly Ser Gly Ala Asp Tyr Ser Leu Thr Ile Ser Ser
                 85                  90                  95

Leu Glu Ser Glu Asp Phe Ala Asp Tyr Tyr Cys Val Gln Tyr Ala Gln
                100                 105                 110

Phe Pro Trp Thr Phe Gly Gly Gly Thr Lys Leu Glu Ile Lys Arg Ala
                115                 120                 125

Asp Ala Ala Pro Thr Val Ser Ile Phe Pro Pro
                130                 135

<210> SEQ ID NO 5
<211> LENGTH: 11
<212> TYPE: PRT
<213> ORGANISM: artificial sequence
<220> FEATURE:
<223> OTHER INFORMATION: heavy chain CDR1

<400> SEQUENCE: 5

Ala Tyr Ser Val Thr Ser Asp Tyr Ala Trp Asn
 1               5                  10

<210> SEQ ID NO 6
<211> LENGTH: 16
<212> TYPE: PRT
<213> ORGANISM: artificial sequence
<220> FEATURE:
<223> OTHER INFORMATION: heavy chain CDR2

<400> SEQUENCE: 6

Tyr Ile Ser Tyr Ser Gly Thr Thr Arg Tyr Asn Pro Ser Leu Lys Ser
 1               5                  10                  15

<210> SEQ ID NO 7
<211> LENGTH: 7
<212> TYPE: PRT
<213> ORGANISM: artificial sequence
<220> FEATURE:
<223> OTHER INFORMATION: heavy chain CDR3

<400> SEQUENCE: 7

Gln Gly Arg Gly Phe Pro Tyr
 1               5

<210> SEQ ID NO 8
<211> LENGTH: 11
<212> TYPE: PRT
<213> ORGANISM: artificial sequence
<220> FEATURE:
<223> OTHER INFORMATION: light chain CDR1

<400> SEQUENCE: 8

His Ala Ser Gln Asp Ile Asn Ser Asn Ile Gly
 1               5                  10

<210> SEQ ID NO 9
<211> LENGTH: 7
<212> TYPE: PRT
<213> ORGANISM: artificial sequence
<220> FEATURE:
<223> OTHER INFORMATION: light chain CDR2
```

```
<400> SEQUENCE: 9

His Gly Thr Asn Leu Glu Asp
1               5

<210> SEQ ID NO 10
<211> LENGTH: 9
<212> TYPE: PRT
<213> ORGANISM: artificial sequence
<220> FEATURE:
<223> OTHER INFORMATION: light chain CDR3

<400> SEQUENCE: 10

Val Gln Tyr Ala Gln Phe Pro Trp Thr
1               5

<210> SEQ ID NO 11
<211> LENGTH: 21
<212> TYPE: PRT
<213> ORGANISM: Homo sapiens

<400> SEQUENCE: 11

Val Arg Ala Cys Gly Ala Asp Ser Tyr Glu Met Glu Glu Asp Gly Val
1               5                   10                  15

Arg Lys Cys Lys Lys
            20

<210> SEQ ID NO 12
<211> LENGTH: 23
<212> TYPE: DNA
<213> ORGANISM: artificial sequence
<220> FEATURE:
<223> OTHER INFORMATION: primer

<400> SEQUENCE: 12
catggctaca tgctgacagc cta                                              23

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
ccagagttcc aggtcactgt cact                                             24

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
acacgactga ggcacctcca                                                  20

<210> SEQ ID NO 15
<211> LENGTH: 34
<212> TYPE: DNA
<213> ORGANISM: artificial sequence
<220> FEATURE:
<223> OTHER INFORMATION: primer

<400> SEQUENCE: 15
cgcggatcca cagcctactg atgatcagtc gatg                                  34
```

```
<210> SEQ ID NO 16
<211> LENGTH: 24
<212> TYPE: DNA
<213> ORGANISM: artificial sequence
<220> FEATURE:
<223> OTHER INFORMATION: primer

<400> SEQUENCE: 16
ccagggtcac catggagtta gttt                                      24

<210> SEQ ID NO 17
<211> LENGTH: 23
<212> TYPE: DNA
<213> ORGANISM: artificial sequence
<220> FEATURE:
<223> OTHER INFORMATION: primer

<400> SEQUENCE: 17
tggatggtgg gaagatggat aca                                       23
```

ANTI-EFGRV3 MONOCLONAL ANTIBODY

FIELD OF THE INVENTION

The present invention relates to the field of the medicine. More particularly, the present invention relates to the specific monoclonal antibody binding to epidermal growth factor receptor variant type III (EGFRvIII) and the uses thereof. The monoclonal antibody of the present invention can effectively bind to epidermal growth factor receptor variant type III (EGFRvIII) or partially bind to the epidermal growth factor receptor (EGFR) over-expressed in cells, but not bind to EGFR normally-expressed in cells. The antibodies of the present invention can be used to treat tumor cell lines with EGFRvIII expression.

BACKGROUND OF THE INVENTION

The epidermal growth factor receptor (EGFR) is the 170 kilodalton membrane glycoprotein product of the proto-on-cogen c-erb B[1]. The EGFR gene is the cellular homolog of the erb B oncogene originally identified in avian erythroblas-tosis viruses[1-2]. Activation of this oncogene by gene amplification has been observed in a variety of human tumors[3-6].

EGFR has been demonstrated to be overexpression on many types of human solid tumors[7], including lung, colon, breast, gastric, brain, bladder, head and neck, ovarian, kidney and prostate carcinomas[7]. One major difference between v-erb B oncogenes and the normal EGFR gene is that the viral oncogenes are amino-truncated versions of the normal receptor: they lack most of the extracytoplasmic domain but remain the transmembrane and tyrosine kinase domains[8-11]. This results in a protein that is unable to bind epidermal growth factor (EGF) but can still phosphorylate other substrates[14-15].

A variety of genetic alterations can occur in viral erb B oncogenes, e.g. amino acid substitutions and deletions in the carboxy terminus of the gene. However, available evidence argues that the amino truncation is critical to carcinogenesis. Amino truncations are a feather of all v-erb B oncogenes, including those that arise by promoter insertion or retroviral transduction[13, 16]. In contrast, carboxy-terminal deletions appear to be associated only with tumors that arise through retroviral transduction and seem to determine host range and tumor type specificity[11, 15]. Transfection experiments with amino-truncated avian c-erb B genes or viral oncogene-human EGF receptors demonstrate that this deletion is sufficient alone to create cell transformation[16-17].

Amplification of the EGFR gene occurs in 40% of the malignant human gliomas. Rearrangement of the receptor gene is evident in many of the tumors with gene amplification[3-7]. The structural alterations seem to preferentially affect the amino terminal half of the gene[6, 18].

There are eight major variants of EGFR that are known: 1) EGFRvI lacks a majority of the extracellular domain of EGFR. 2) EGFRvII consists of an 83 aa in-frame deletion in the extracellular domain of EGFR. 3) EGFRvIII consists of a 267 aa in-frame deletion in the extracellular domain of EGFR. 4) EGFRvIV contains deletions in the cytoplasmic domain of EGFR. 5) EGFRvV contains deletions in the cytoplasmic domain of EGFR. 6) EGFR.TDM/2-7 contains a duplication of exons 2-7 in the extracellular domain of EGFR. 7) EGFR.TDM/18-26 contains a duplication of exons 18-26 in the tyrosine kinase domain of EGFR. 8) In addition, there is a second, rarer, EGFRvIII mutant (EGFRvIII/Δ12-13) that possesses a second deletion that introduces a novel histidine at the junction of exons 11 and 14[24].

EGFRvIII is the most commonly occurring variant of the epidermal growth factor (EGF) receptor in human cancers[24]. During the process of gene amplification, a 267 amino acid deletion occurs in the extracellular domain creating a novel junction (glycine). EGFRvIII is not known to be expressed on any normal tissues[19, 20]. Yet, EGFRvIII shows significant expression in tumor cells, e.g., 27~76% breast cancer biopsies express EGFRvIII[21], 50~70% gliomas express EGFRvIII[19, 22], 16% NSCL cancers express EGFRvIII[23], and 75% ovarian cancers express EGFRvIII[22].

A method of treating cancers which over-express EGFRvIII involved the use of a tumor-specific ribozyme targeted specifically to the variant receptor which did not cleave normal EGFR. The ribozyme was found to significantly inhibit breast cancer growth in athymic nude mice[25].

In addition, the substitution of the deleted 267 amino acid with a Glycine creates a unique junction that may be capable of antibody targeting. Further, in view of EGFRvIII's expression in certain tumors and its lack of expression in normal tissues, EGFRvIII may be an ideal target for drug targeting in tumor therapy. In particular, EGFRvIII would appear to be an ideal candidate for immunoconjugate therapy of tumors. The monoclonal antibody against EGFRvIII (or the immunoconjugate of anti-tumor agent and toxic) can cause antibody-dependent cell-mediated cytotoxicity (ADCC) or kill the cells in vivo, leading to eliminating the tumor cells with EGFRvIII expression.

At present, a number of antibodies directed against EGFR have been obtained at home and abroad, but these antibodies still are not very ideal because of causes like their having no or less specificity for EGFRvIII.

Therefore, in the art it is urgent to produce a specific monoclonal antibody directed against EGFRvIII with highly specificity for this receptor but not the wtEGFR and with other excellent characteristics, leading to developing a new drug with distinct therapeutic effect.

SUMMARY OF THE INVENTION

The purpose of this invention is to provide an anti-EGFRvIII specific monoclonal antibody.

Another purpose of this invention is to provide a method for preparing the said anti-EGFRvIII specific monoclonal antibody.

Another purpose of this invention is to provide a pharmaceutical composition containing said anti-EGFRvIII specific monoclonal antibody.

The first aspect of the present invention is to provide a monoclonal antibody $V_H$ chain. The complementarity-determining region (CDR) of the said heavy chain comprises the amino acid sequence of the CDR selected from the following group:
CDR1 as shown in SEQ ID NO: 5,
CDR2 as shown in SEQ ID NO: 6, and
CDR3 as shown in SEQ ID NO: 7.

In another preferred example, the said $V_H$ chain comprises the amino acid sequence set out in SEQ ID NO: 2.

The second aspect of the present invention is to provide a monoclonal antibody $V_L$ chain. The complementarity-determining region (CDR) of the said light chain comprises the amino acid sequence of CDR selected from the following group:
CDR1 as shown in SEQ ID NO: 8,
CDR2 as shown in SEQ ID NO: 9, and
CDR3 as shown in SEQ ID NO: 10.

In another preferred example, the said $V_L$ chain comprises the amino acid sequence set out in SEQ ID NO: 4.

The third aspect of the present invention is to provide monoclonal antibody or its conjugate, the $V_H$ chain of the said antibody comprises the amino acid sequence set out in SEQ ID NO: 2, and its $V_L$ chain comprises the amino acid sequence set out in SEQ ID NO: 4.

In another preferred example, the said antibody binds to epidermal growth factor receptor variant type III (EGFRvIII) and binds to EGFR over-expressed in cells, but not binds to EGFR normally-expressed in cells.

More preferably, the said antibody binds to A431 cells and U87-EGFRvIII cells, but does not bind to U87 cells.

In another preferred example, the said antibody can be mouse antibody, humanized antibody or chimeric antibody.

In another preferred example, the said conjugate is the conjugate coupling antibody with antitumor agent or toxin (such as diphtheria toxin, ricin, ectotoxin of *Pseudomonas aeruginosa*).

The fourth aspect of this invention is to provide a nucleic acid molecule (such as DNA); the said coding sequence is selected from the following protein:

Monoclonal antibody $V_H$ chain said in the first aspect of this invention;

Monoclonal antibody $V_L$ chain said in the second aspect of this invention;

Monoclonal antibody said in the third aspect of this invention.

In another preferred example, the said nucleic acid molecule is selected from the following DNA sequence: SEQ ID NO: 1, 3, 11 or 13.

The fifth aspect of this invention is to provide a pharmaceutical composition, which contains a monoclonal antibody and a pharmaceutically acceptable carrier, the said monoclonal antibody $V_H$ chain and the said monoclonal antibody $V_L$ chain comprise complementarity-determining region set out in SEQ ID NO: 5-7 and SEQ ID NO: 8-10 respectively.

In another preferred example, the said monoclonal antibody $V_H$ chain comprises the amino acid sequence set out in SEQ ID NO: 2, and its $V_L$ chain comprises the amino acid sequence set out in SEQ ID NO: 4.

The sixth aspect of this invention is to provide the application of the said monoclonal antibody or its conjugate, wherein they are used to prepare compositions, the said composition is used in: (a) inhibiting or killing the growth of cells expressing the epidermal growth factor receptor variant type III; or (b) inhibiting the growth of cells over-expressing epidermal growth factor receptor.

In another preferred example, the said cells are tumor cells, such as liver cancer cells, lung cancer cells.

The seven aspect of this invention is to provide (a) a method of the growth inhibiting or killing of the cells expressing epidermal growth factor receptor variant type III; or (b) a method of inhibiting the growth of cells over-expressing epidermal growth factor receptor, the said method includes: providing the said monoclonal antibody or its conjugate to the subject who need to be treated.

The preferred embodiment, the said subject is mammal, such as human, mouse or rat.

A: C225 binding to A431 cells;
B: 12H23 binding to A431 cells;
C: C225 binding to U87-EGFRvIII cells;
D: 12H23 binding to U87-EGFRvIII cells;
E: C225 binding to U87 cells;
F: 12H23 binding to U87 cells.

Figure 8:
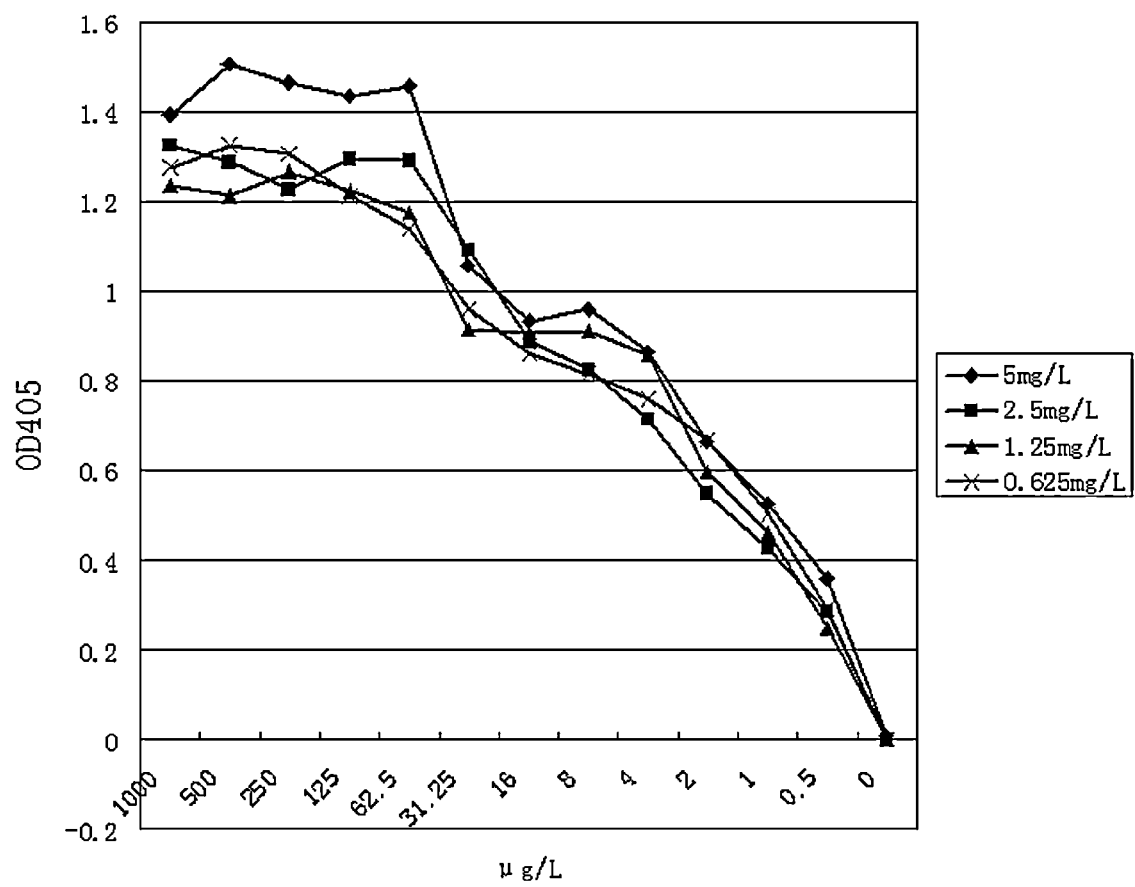

FIG. 8 shows the affinity test of 12H23 with rEGFRvIIIex protein antigen.

Figure 9:
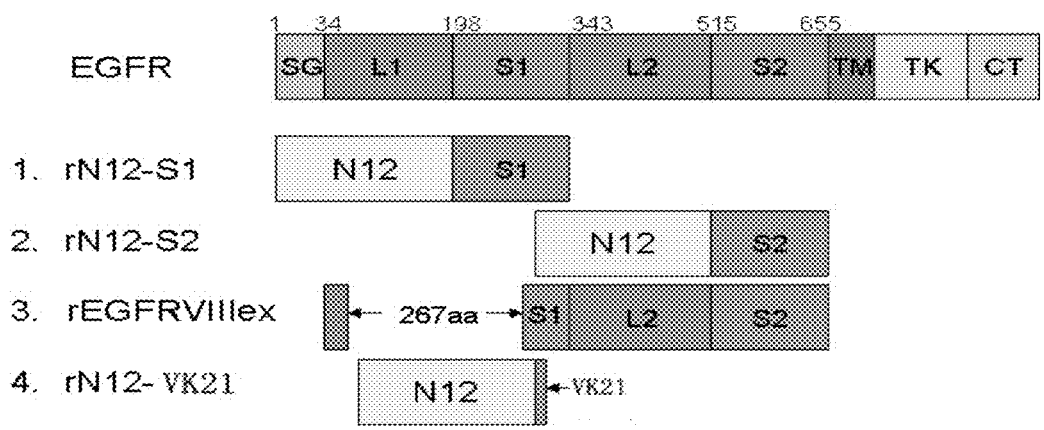

FIG. 9 shows the sequence structure of each recombinant protein.

Figure 10:
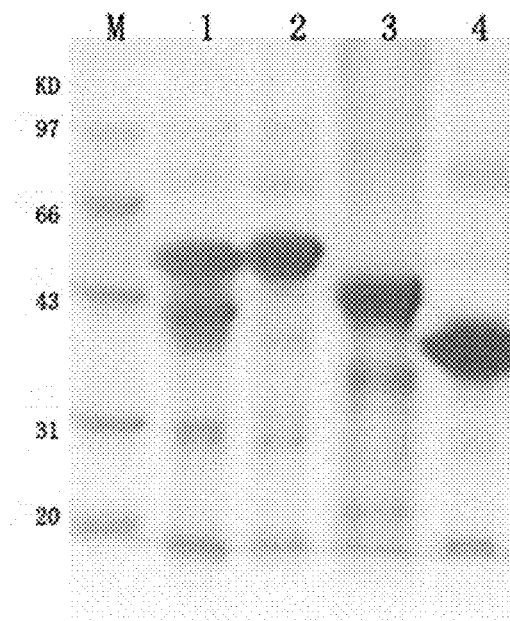

FIG. 10 is SDS-PAGE analysis of the recombinant proteins. The lanes represent respectively: lane M: molecular weight marker; lane 1: rN12-S1; lane 2: rN12-S2; lane 3: rEGFRvIIIex; lane 4: rN12-VK21.

Figure 11:
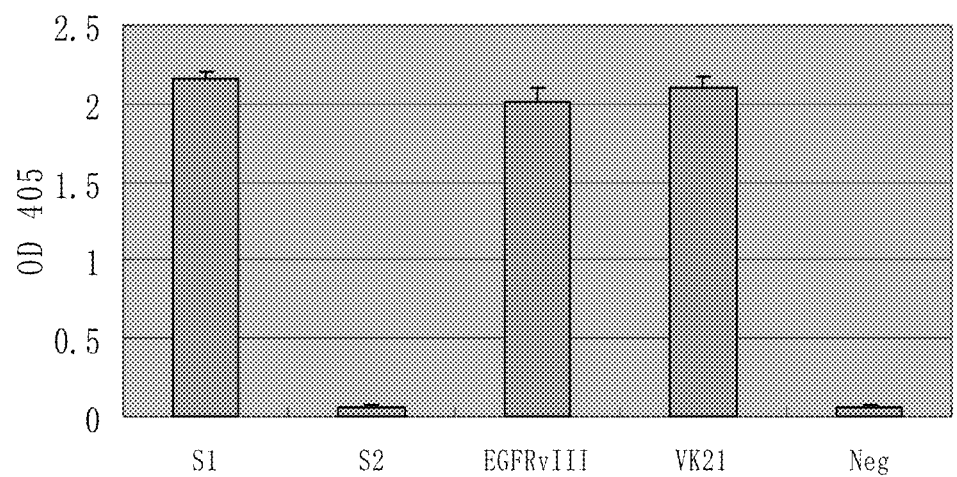

FIG. 11 display the results of the EILSA analysis of 12H23 binding epitope. S1 represents rN12-S1; S2 represents rN12-S2; EGFRvIII represents recombinant EGFRvIII extracellular region protein; VK21 represents rN12-VK21; Neg represents blank control.

Figure 12:
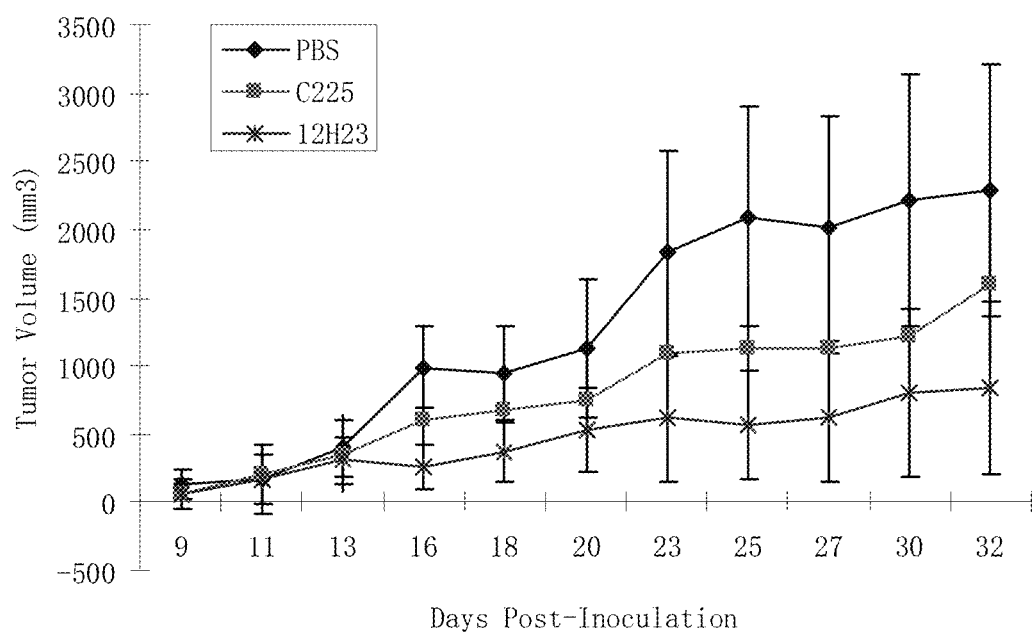

FIG. 12 shows the growth inhibition effect of monoclonal antibody 12H23 on tumor xenografts in nude mice.

FIG. 13 shows the nucleotide sequences and amino acid sequences of the heavy chain of monoclonal antibody 12H23 (underlined part represents CDR).

FIG. 14 shows the nucleotide sequences and amino acid sequences of 12H23 monoclonal antibody light chain (underlined part represents CDR).

FIG. 15 is a schematic presentation of pH and pK of plasmid.

Figure 16:
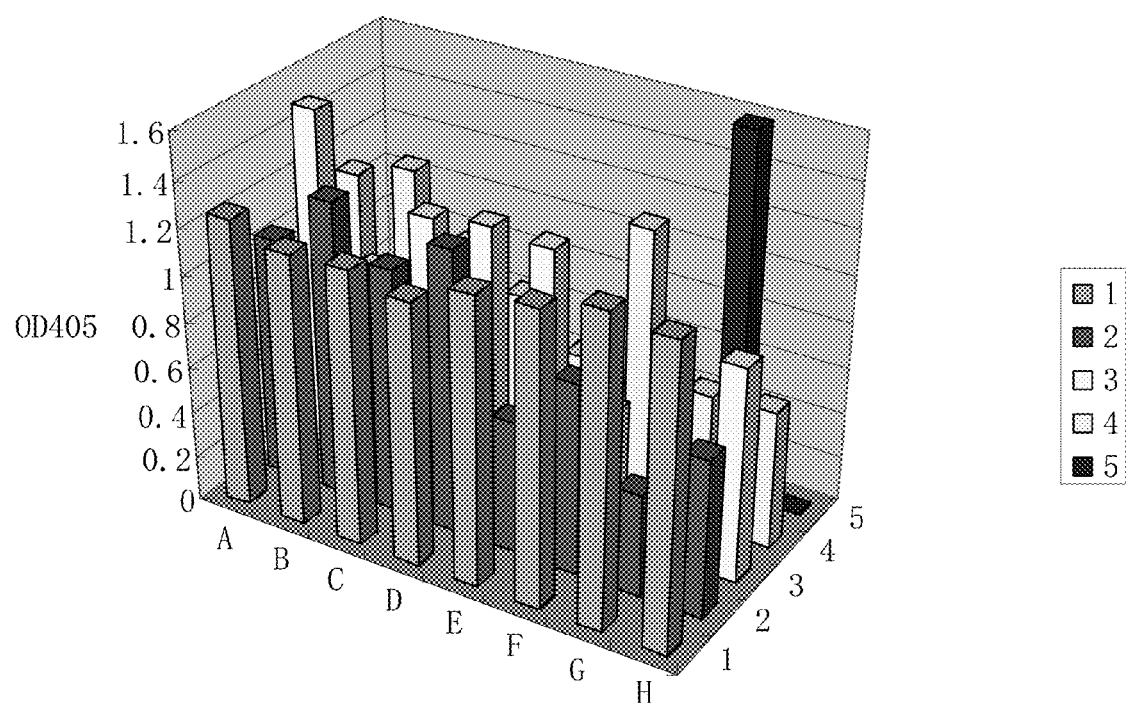

FIG. 16 shows human/mouse chimeric antibody CH12 binding to the recombinant EGFRvIII extracellular protein. 1-5 in the figure shows the individual cell clone expressing CH12.

Figure 17:
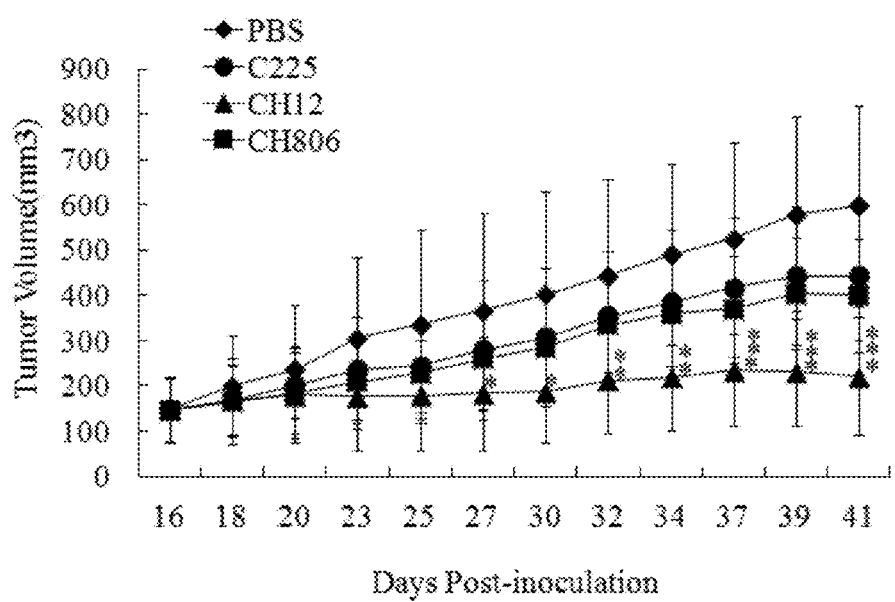

FIG. 17 shows the growth inhibition effect of chimeric antibody CH12 on tumor xenografts in nude mice.

DETAILED DESCRIPTION

The inventor has successfully obtained a monoclonal antibody with high specificity to EGFRvIII through wide and thorough study. The monoclonal antibody can effectively bind to epidermal growth factor receptor variant type III (EGFRvIII) or partially bind to the epidermal growth factor receptor (EGFR) over-expressed in cells, but not bind to EGFR normally-expressed in cells. Furthermore, the antibody said in the present invention has obvious therapeutic effect on tumor cell lines expressing EGFRvIII. This invention was finished on this basis.

This invention provides a kind of recombinant anti-EGFRvIII monoclonal antibody. The said antibody can be mouse antibody, humanized antibody or chimeric antibody. For example, the humanized antibody can be composed of the constant region of human antibody (such as human constant region IgG1-Fc), the heavy chain variable region and the light chain variable region of this invention.

The present invention also provides an amino acid sequence of anti-EGFRvIII monoclonal antibody, and its variable region chains, and other proteins or fusions bearing these chains. Particularly, this invention includes proteins or protein conjugates or fusions which have light chain with hyper variable region (complementarity determining region, CDR) and heavy chain with hyper variable region (complementarity determining region, CDR) (that is immune conjugate and fusion expression product), as long as this hyper variable region shares the same or at least 90% homology with the light chain and the heavy chain hyper variable region of this invention, more perfectly, at least 95% homology.

The antigenic binding properties of the antibody can be described by three special regions of the heavy chain variable region and the light chain variable region, called hyper variable region (CDR) which separating the chain into four frame regions (FR). The amino acid sequences of these four FRs are relatively more conservative and do not participate in binding reaction directly. These CDRs form cyclic structure and are spatially closed each other through the β-folds formed by the FRs. CDRs of heave chain and CDRs of corresponding light chain form the antigen-binding site of the antibody. The amino acids that form the FR or CDR region can be determined by comparing the amino acid sequences of the same type of antibody.

In addition, recent studies show that the binding dynamics of the relevant structure formed by variable region of light chain is smaller than that formed by the corresponding variable region of heavy chain; the separated variable region of heavy chain itself has antigen binding activity.

The identified hyper variable regions or complementarity determining regions (complementarity determining region, CDR) of V chain are very interesting, because they are at least partially involved in antigen-binding. Therefore, the present invention includes those molecules comprising the CDR-bearing light chain variable regions and the CDR-bearing heavy chain variable regions of monoclonal antibodies, as long as its CDR shares more than 90% homology with the said identified CDR (Perfectly more than 95% homology, the best perfectly more than 98% homology).

This invention not only comprises intact monoclonal antibodies, but also comprises immunoreactive antibody fragments, such as Fab or (Fab')$_2$ fragments; heavy chain of antibodies; light chain of antibodies; genetically-engineered single chain Fv molecules; or chimeric antibodies, such as antibody having the binding specificity of mouse antibody while retaining partial human antibody.

The present invention also provides DNA molecules which encode the above said monoclonal antibodies or its fragments. The full-length nucleotide sequence of the monoclonal antibodies said in the present invention or its fragments could be obtained by using PCR amplification method, recombination method or synthetic method. A feasible method is to synthesize relevant sequences by synthetic method, especially when the fragments are short. Usually, long fragments are obtained through firstly synthesizing a lot of short fragment and then linking them together. In addition, a single chain antibody can be made by fusing a coding sequence of light chain with a coding sequence of heavy chain.

Once the relevant sequence is obtained, it can be abundantly amplified by recombination method. Usually, the relevant sequences are cloned into vector and then transformed into cells. After that, the relevant sequences are separated from the reproduced host cells by conventional method.

At present, the DNA sequence encoding the protein (or its fragment, or its derivatives) of this invention could be obtained by chemosynthesis methods completely. Then the said DNA sequence is introduced into all kinds of existing DNA molecules (or vector) and cells known in the art. In addition, mutants can be introduced into the protein sequence said in the present invention through chemosynthesis methods.

The present invention also involves vectors comprising the above-mentioned appropriate DNA sequence and appropriate promoter or control sequence. These vectors could be used to transform appropriate host cells to express the protein.

The said host cell can be prokaryotic cells such as bacterial cells; or lower eukaryotic cells such as yeast cell; or higher eukaryotic cell such as mammalian cells. The representative example is as follows: *Escherichia coli, Streptomyces*; Bacterial cell of *Salmonella typhimurium*; fungal cell such as yeast; insect cell of *Drosophila* S2 or *Drosophila* Sf9; animal cells like CHO, COST and 293.

The host cells are transformed with recombinant DNA by the routine technique which is known to the technical persons in the art. When the host cell is prokaryote such as *E. coli*, the competent cells which can accept DNA can be harvested after the cells are in the exponential growth phase and treated by $CaCl_2$. The procedure is well known in the art. Using $MgCl_2$ is another method. Transformation can also be done by the electroporation method if necessary. When the host cell is eukaryote, the following DNA transfection methods can be selected: calcium phosphate precipitation method, routine mechanical method such as microinjection method, electroporation method, liposome packaging method and so on.

The obtained transformant can be cultured by the conventional method to express the polypeptide which is encoded by the gene of the present invention. When culturing the host cells, culture medium could be selected from the routine culture medium according to the used host cells. The host cells are cultured under the suitable growth condition. After the host cells growing to an appropriate density, the selected promoter is induced by the suitable means (such as temperature conversion method or chemical induction method) and the cells will be cultured for a period of time.

In the above mentioned methods, the recombination polypeptide can be expressed in the cell or on the cell membrane, or secreted out of the cell. The recombinant proteins can be separated or purified by various separation methods according to its physical characteristics, chemical characteristics or other characteristics if necessary. These methods are well known by the technical persons in the art. These methods include but not limited: treated by routine renaturation, treated by protein precipitating agent (salting-out method), centrifugation, osmotic sonication, sonication, ultracentrifugation, molecular sieve chromatography (gel filtration), adsorption chromatography, ion exchange chromatography, high-performance liquid chromatography (HPLC) and other various liquid chromatographic technique as well as their combination.

The present invention also provides a composition. The preferred embodiment, the said composition is pharmaceutical composition which contains the above mentioned monoclonal antibody or immune conjugate, and a pharmaceutically acceptable vector. Usually, these substances can be prepared in the nontoxic, inactive and pharmaceutically acceptable aqueous medium, wherein pH is usually about 5-8 and the preferred pH is about 6-8, although pH value can be changed according to the characteristics of the prepared substance and the treated diseases. The prepared pharmaceutical composition can be administrated by conventional method, including (but not limited): intratumoral, intraperitoneal, intravenous or topical administration.

The pharmaceutical composition of the present invention can be used to prevent and treat tumor directly. In addition, other therapeutic agent can be used simultaneously.

The pharmaceutical composition of this invention contains the monoclonal antibody (or its conjugate) said in this invention and pharmaceutically acceptable vector or excipient at a safe and effective dosage (such as 0.001-99 wt %, the preferred amount is 0.01-90 wt %, the further preferred amount is 0.1-80 wt %). This kind of vector includes (but not limited): saline, buffer, dextrose, water, glycerin, ethanol and its combination. Pharmaceutical preparations should be matched with the mode of administration. The pharmaceutical composition of this invention can be made into the injection form, for example, prepared by conventional method using saline or water containing dextrose and other adjuvant. The pharmaceutical composition such as injection, solution should be prepared under aseptic condition. Dosage of active component is therapeutically effective, for example, about 1 mg/kg body weight-5 mg/kg body weight per day. In addition, the polypeptide of this invention can also used together with other therapeutic agents.

When using pharmaceutical composition, immune conjugate with safe and effective dose is applied on the mammal, usually the safe and effective dose is at least about 10 mg/kg body weight, and is not more than about 8 mg/kg body weight in most cases, the preferred dosage is about 10 mg/kg body weight-1 mg/kg body weight. Of course, route of administration, patient health status and other factors should be considered when making the practical dosage, all these are within skill range of the skilled doctor.

The prominent advantages of this invention are:

(a) Specificity and physiological activity of the present invention monoclonal antibody are improved significantly. The monoclonal antibodies can effectively bind to EGFRvIII or partially bind to EGFR over-expressed in cells, but not bind to EGFR normally-expressed in cells.

(b) The affinity and tumor inhibitory rate of the antibodies said in this invention are higher than the existing antibody (such as CH806 antibody) and their antibody amino acid sequences (especially CDR region) are different.

So, the monoclonal antibodies said in the present invention with the high affinity and high specificity may have important value in clinical practice.

The present invention will be further explained with the following examples. It should be understood that these examples are used to explain this invention but not to restrict this invention. The experimental method without indicated reaction conditions in the following examples usually utilize the conventional reaction conditions, such as the condition described by Sambrook et al. in molecular cloning: the manual of research laboratory (New York: Cold Spring Harbor Laboratory Press, 1989), or the reaction condition suggested by the manufacturer. The percentage and the number of shares are calculated by weight unless other declaration.

Example 1

Preparing Antigen 1.1 Prokaryotic Expression and Purification of EGFRvIII Extracellular Region
1.1.1 Vector Construction and Determination EGFRvIIIex amplified products with BamHI and SaiI restriction site in the both ends were obtained by PCR method utilizing pLNRNL (encoding full-length EGFRvIII, obtained from Ludwig Institute, San Diego, Calif.) as template, and the target fragment was obtained by BamHI and SaII double digestion. And thus the target fragment was cloned into the expression vector pET28a which is digested by the enzymes BgIII and SaII. The positive clones were screened by the resistance of kanamycin, and identified by BgIII and SaII double digestion.

1.1.2 Expression Screening in E. coli

The correct recombinant plasmid was transformed into E. coli BL21 (DE3), BL21 (DE3)-RP, HMS174 (DE3) separately, (brought from Novagen company), and was cultured overnight at 37° C. in LB medium with the kanamycin. Selected individual clone was cultured with shaking until OD value reached 0.6-0.8, and IPTG was then added to the culture at a final concentration 1 mM. The bacteria are harvested after induced at 30° C. for 4 h, the precipitate is obtained through centrifugation, and the precipitate is used to analysis the protein expression level by SDS-PAGE electrophoresis.

1.1.3 Induction Conditions Analysis for the Fusion Protein

In order to improve the expression level of target protein, a series of induced conditions were tested in the experiment. (1) Induction hours: inoculate the bacteria in LB medium growing at 37° C. with vigorous shaking until an OD value of 0.6-0.8 is reached. The expression was induced by the addition of IPTG at a final concentration of 1 mM and the cultures were incubated for an additional 1, 2, 3, 4, 5, 6 h respectively. (2) The concentration of IPTG: after the expression strain was cultured to an OD value of 0.6-0.8, IPTG was add at a final concentration of 0.2, 0.5, 0.8 or 1 mM respectively and the bacteria were shaken for 4 h at 30° C. The cells were harvested. (3) Induction temperature: after the expression strain was cultured until OD reached 0.6-0.8, IPTG was added to 1 mM as final concentration and the bacteria were induced for 4 hours at 37° C., 30° C., or 25° C. respectively. The cells were finally harvested.

1.1.4 Determine Fusion Protein Expression

After the cells were induced according to above-mentioned conditions, the cell pellet was collected, resuspended in 10 volumes of buffer A containing 1 mM PMSF (50 mM NaH$_2$PO4, 300 mM NaCl, 10 mM imidazole pH 8.0) and sonicated for 99×3 s with 10 s pauses and 4 cycles. The lysate was kept on ice at all times. The lysate was centrifuged at 12,000×g, 4° C. for 15 min. The supernatant and the pellet were collected respectively for the SDS-PAGE electrophoresis. The SDS-PAGE gel was observed after it was stained with 0.25% Coomassie blue for 3 h and then decolorized.

1.1.5 Washing and Degeneration of the Inclusion Body

The precipitation was resuspended thoroughly in washing buffer I (100 mM NaH$_2$PO4, 10 mM Tris-C1, 2M urea, pH 8.0) after the cell pellet was ultrasonically lysed and centrifuged. After the resulted lysate was stirred at 4° C. for 30 min and then centrifuged for 15 minutes (4° C., 12000 g), the precipitation was collected. Washing liquid II was added (100 mM NaH$_2$PO4, 10 mM Tris-HCl, 2M GuHCl, pH 8.0) and last step was repeated. The purified inclusion body was obtained. The inclusion body was resuspended in a 8M urea solution (100 mM NaH$_2$PO4, 10 mM Tris-HCl, 8M urea, pH 8.0) and ultrasonicated on the ice, and centrifuged (4° C., 12000 g) for 15 min. The supernatant was obtained while the precipitation was abandoned.

1.1.6 Purification of the Fusion Protein

The supernatant was mixed with Ni-NTA agarose at 4° C. for 1 hour or overnight and the mixture was then loaded into an affinity column. The flow-through was collected. The column was washed 3 times with 4 ml buffer C (100 mM $NaH_2PO_4$, 10 mM Tris-HCl, 2M urea, pH 6.3) and eluted 4 times with 0.5 ml buffer D (100 mM $NaH_2PO_4$, 10 mM Tris-HCl, 2M urea, pH 5.9) and 4 times with 0.5 ml buffer E (100 mM $NaH_2PO_4$, 10 mM Tris-HCl, 2M urea, pH4.5). The fractions were collected and the purity was analyzed by 12% SDS-PAGE electrophoresis. The protein concentration was measured at 280 nm (A280).

1.1.7 Refolding of the Fusion Proteins

The purified protein was added dropwisely into 10 volumes of pre-cooling buffer solution (25 mM Tris-HCl, 0.1M NaCl, 10% glycerin, 1.0M urea, 0.01M arginine, 1 mM reductive glutathione, 0.5 mM oxidative glutathione, pH 8.0) and incubated at 4° C. for 24 h. The protein solution was transferred to a dialysis bag and then successively dialysed with 0.5M, 0.25M and 0.125M urea buffer (PBS, pH 7.4) for more than 4 h in each buffer. Finally, the protein solution was dialysed in large volume of PBS at 4° C. for 24 h. After that, the protein solution was centrifuged and the supernatant was obtained.

1.1.8 Analysis of the Refolded Protein by Western Blot

The refolded protein run on a 12% SDS-PAGE and the total protein of BL21 (DE3)-RP Bacteria was set as a negative control. The protein in the gel was transferred to a NC (nitrocellulose) membrane. Then the membrane was incubated with rabbit anti-EGFRvIII monoclonal antibody (1/1000 dilution, Zymed Company) overnight at 4° C. After the membrane was washed 3 times×10 min with PBST, it was incubated with HRP-labeled mouse anti-rabbit IgG (1/5000 dilution) for 1 h at 37° C. followed by washing 3 times×10 min with PBST. Finally, the membrane was developed with ECL chemiluminescence agents and exposed to a X-ray film in a darkroom.

Figure 1:
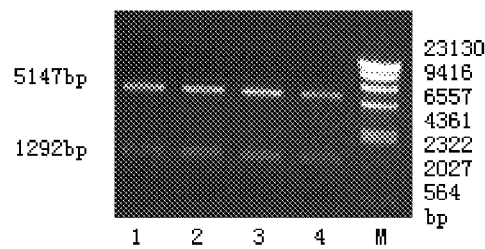
FIG. 1 shows the recombinant plasmid pET28a-EGFRvIIIex digested by BglII and SalI restriction enzyme. The lanes represent respectively: lanes 1-4 is the double digested plasmid; lane M: λHindIII DNA molecular weight marker.

Results:

1. Identification of pET28a-EGFRvIIIex Recombinant Expression Plasmid pET28a-EGFRvIIIex recombinant expression plasmid was digested by BglII and SalI enzyme. As expected, the digested bands were 1292 bp and 5147 bp respectively (see FIG. 1), indicating that the vector was successfully constructed.

2. Purification of EGFRvIII Extracellular Region Protein

Figure 2:
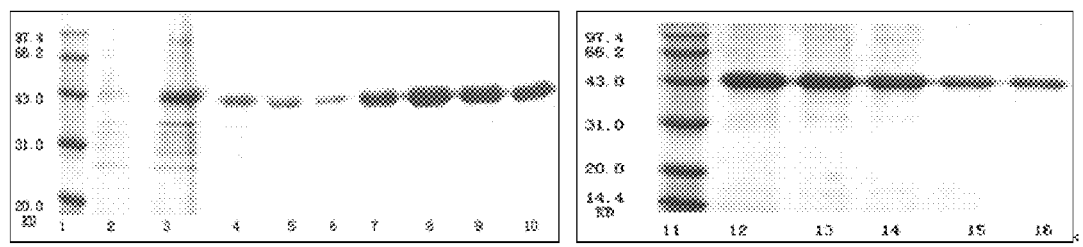
FIG. 2 shows the purification results of EGFRvIII extracellular region protein. The lanes represent respectively: lanes 1 and 11: protein molecular weight marker; lane 2: the precipitate of uninduced bacteria; lane 3: effluent; lanes 4-6: washing solution of buffer C; lanes 7-10: elution of buffer D; lanes 12-16: elution of buffer E.

As shown in FIG. 2, the EGFRvIII extracellular domain (EGFRvIIIex) was purified.

3. Identification of Renatured EGFRvIIIex Protein

Figure 3:
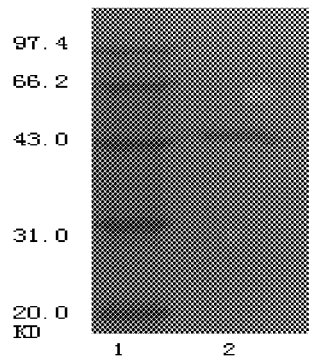
FIG. 3 is SDS-PAGE analysis of the renatured protein. The lanes represent respectively: lane 1: protein molecular weight marker; lane 2: renatured protein.
Figure 4:
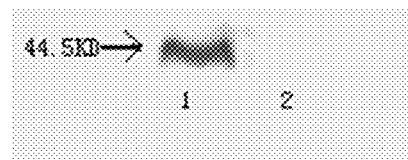
FIG. 4 is Western blot analysis of the renatured protein. The lanes represent respectively: lane 1: renatured protein; lane 2: total protein of BL21 (DE3)-RP bacteria.
Figure 5:
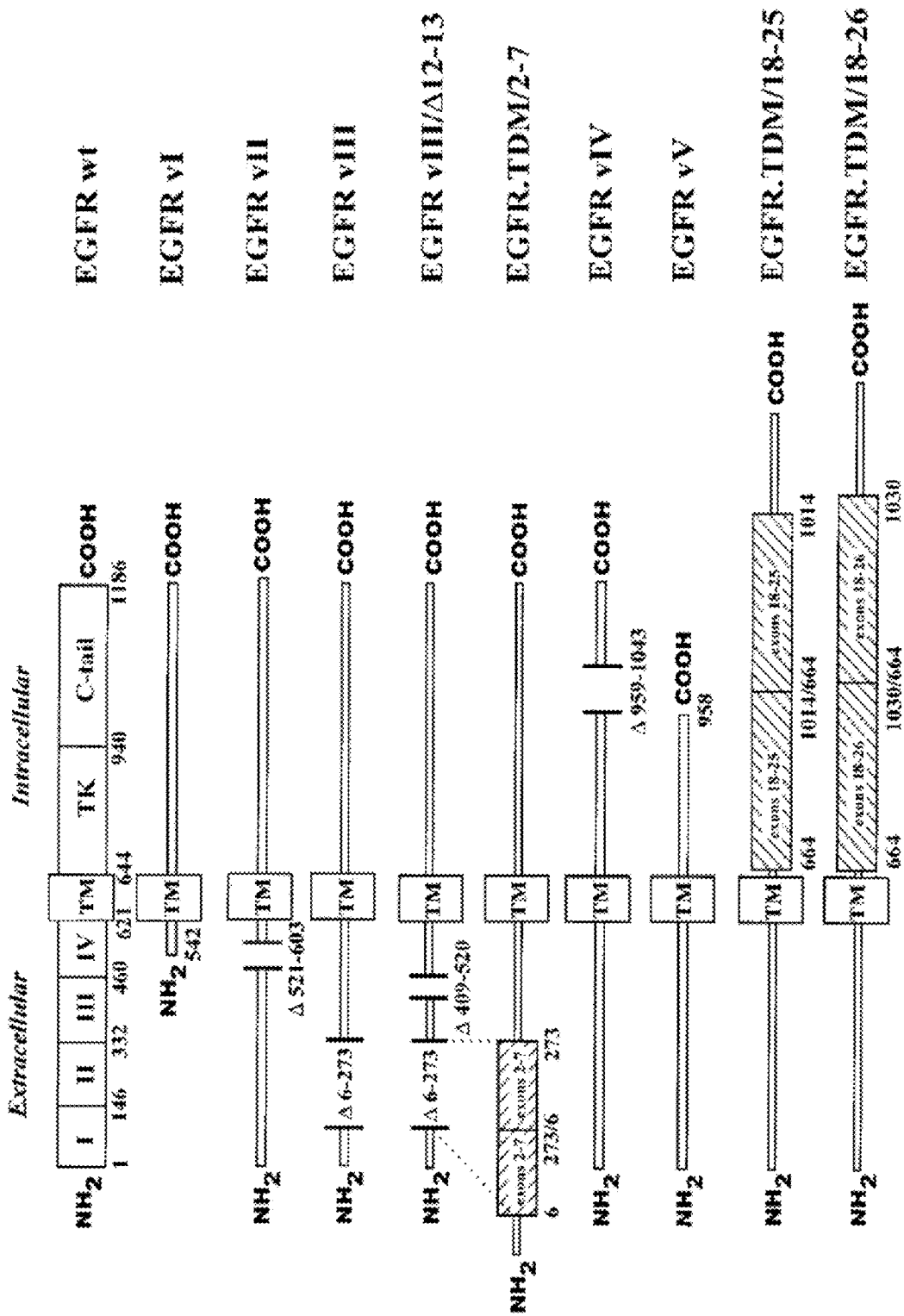
FIG. 5 is a schematic presentation of wild type EGFR and its various mutants.

The results shown in FIG. 3 and FIG. 4 indicated that the purity of EGFRvIIIex protein was very high.

Example 2

Antigen Immunization and Hybridoma Screening 2.1 Immunization (1) Recombinant Protein Immunization After recombinant EGFRvIIIex protein with the same amount of Freund's complete adjuvant (Sigma) were thoroughly emulsified and mixed, 100 µg of the mixture was subcutaneously administered to each 6-week old BALB/c mouse. Recombinant antigens and Freund's incomplete adjuvant were emulsified and mixed 4 weeks later, and 50 µg of the mixture were administered to each mouse by intraperitoneal injection. The immunization was boosted by intraperitoneal injection of the same antigen every 2 weeks. One week after the 4th booster immunization, the antiserum titer was found to be greater than $10^5$ by ELISA test with coated recombinant antigens.

(2) Intrasplenic Injection with Booster Immunization

Three weeks after the last booster immunization, 20 µg of recombinant antigens were used in intrasplenic immunization.

2.2 Establishment of Hybridoma Cell Lines

The spleen of the mouse was taken out under sterile conditions on 4th day after booster immunization through intrasplenic injection. The lymphocytes were separated from the spleen by a 100-mesh strainer and fused with the myeloma cell line SP2/0; the mixture was selectively cultured for 3 days with hypoxanthine, aminopterin and thymidine (HAT). After that a HT (hypoxanthine and thymidine) culture medium was supplemented and then cultured for another week. The positive clones were screened by ELISA with coated recombinant antigens, subcloned for three times by limiting dilution and then cultured for two months to obtain stable hybridoma cell lines.

As a result, multiple positive clones were obtained. Among them clone 12H23 had the highest binding activity.

2.3 Antibody Purification 2.3.1 Primary Purification by Precipitation with Caprylic Acid/Ammonium Sulfate 100 mL of Ascitic fluid was diluted with a two-fold volume of sodium acetate buffer (0.06M, pH 4.0). 4% caprylic acid was dropwisely added while stirring. After 30 min's stirring, the turbid solution was centrifuged at 10000 g for 30 min. After the sediment was removed, the supernatant was dialyzed overnight with phosphate buffer (0.01M, pH 7.4). The dialysate was transferred to a new tube and a same volume of saturated ammonium sulfate was slowly added to the solution followed by incubation for 2 hours. The obtained turbid solution was centrifuged at 10000 g for 10 min. The supernatant was removed and the sediment was dissolved with PBS buffer (0.01M, pH7.4). The dissolved solution is dialyzed with PBS (0.01 M, pH7.4). The PBS buffer was changed twice at an interval of not less than 5 hours. The dialysate was centrifuged at 10000 g for 10 min. The sediment was removed while the supernatant was collected.

2.3.2 Protein G Affinity Purification

Protein G affinity columns were taken out, recovered to the room temperature and balanced with five column volumes of PBS. The monoclonal antibody solution were added to the column and then washed with five column volumes of PBS. The protein was eluted with glycine hydrochloric acid solution (pH2.3, 0.1M). The eluate was neutralized with a 1/10 volume of sodium hydrogen phosphate (1M, pH 9.0). The resulted solution was dialyzed with PBS (0.01M, pH 7.4). The PBS buffer was changed twice with an interval of more than 5 hours. After the dialysate was centrifuged at 10000 g for 10 min, the supernatant was filtrated with 0.22 µm filtration membrane and stored. Thus, the monoclonal antibody solution was obtained.

Antibodies with a purity of more than 95% were obtained after purified by the above mentioned procedures.

2.4 Determining the Isotype of Monoclonal Antibody 12H23

The wells of a 96-well microtiter plate were coated with 50 µl of rEGFRvIIIex diluted to 1.0 mg/L with carbonate buffer ($NaHCO_3$ PH 9.6) and incubated overnight at 4° C. for 24 hours. The wells were added with 350 µl of PBS containing 5% of skimmed milk powder and incubated overnight. Then the plates were washed with PBS twice and added with 50 µl of 12H23 monoclonal antibody at an initial concentration of 1 mg/L. The plates were incubated with antibodies for 1 hour at 37° C. and washed thrice with PBS. Then the plate were added with 100 μL of goat anti-mouse isotype-specific antibodies polyclonal antibody (1/1000 dilution), and incubated at 37° C. for 1 hour. After washing thrice with PBS, the plates were added with the HRP-labeled donkey anti-goat polyclonal antibody and incubated at 37° C. for 30 min. The plates were then washed 5 times with PBS followed by incubation with ABTS substrate for 15 min. The absorbance value was measured at 405 nm with a microplate reader.

Figure 6:
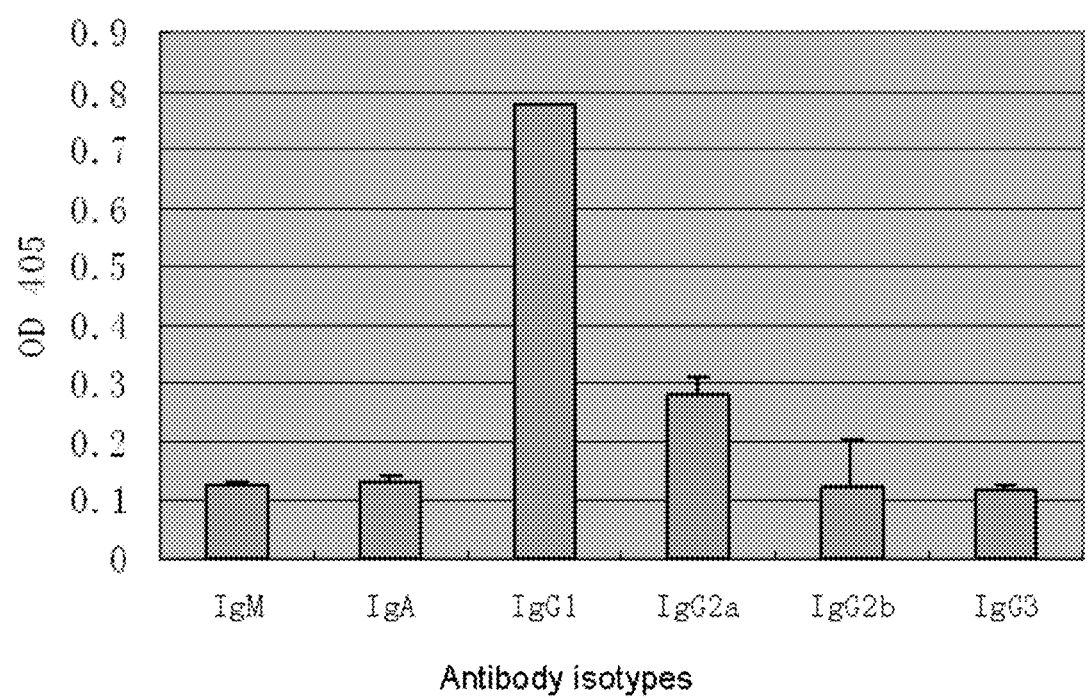
FIG. 6 is ELISA analysis of 12H23 antibody isotype.
Figure 7:
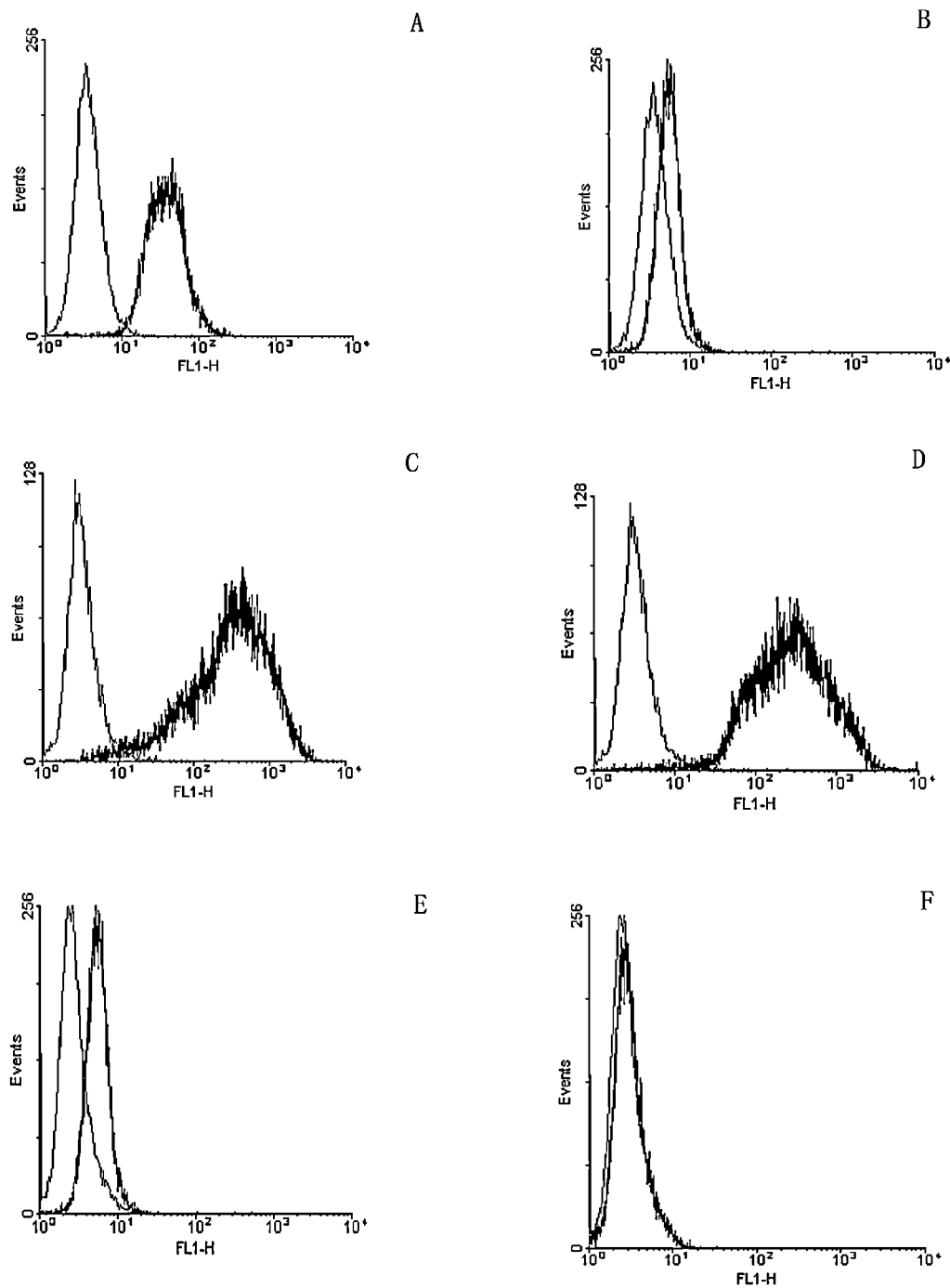
FIG. 7 is the flow cytometry analysis of the antibody 12H23 of the present invention and the control antibody C225 respectively with A431 cells (over-expressing EGFR), U87-EGFRvIII cell (stably over-expressing EGFRvIII) and U87 cell (normally-expressing EGFR). Wherein, each graph is as follows.

As shown in FIG. 6, the isotype of antibody 12H23 was IgG1.

Example 3

Binding Ability Assay of Monoclonal Antibody 3.1 Binding Specificity of 12H23 Against the Receptor Analyzed by FACS Assay
Vector Construction Cell: U87 cells (human glioblastoma cells with normally-expressed EGFR, obtained from ATCC cell bank), U87-EGFRvIII cells (U87 cells transfected with pLERNL vector), and A431 cells (human epidermal squamous cell carcinoma cell lines over-expressing wtEGFR, obtained from ATCC cell bank).

Antibodies: the antibody 12H23 prepared in the example 2 and commercial C225 monoclonal antibodies (as control) both at a concentration of 2 mg/ml were diluted 1:100.

1) Cells in exponential phase were seeded into a 6-well culture plate at a cell density of 90% and cultured overnight at 37° C. in an incubator.

2) The next day, the cells were treated with 10 mM of EDTA, centrifuged at 5000 rpm×3 min and collected into an Eppendorf tube (2 ml).

3) Cells were re-suspended with 0.5-1 ml of PBS, fixed with 4% paraformaldehyde and incubated at 37° C. for 10 min.

4) The cells were chilled on ice for 1 min.

5) The cells were centrifuged at 5000 rpm×3 min and the supernatant was removed.

6) The cells were resuspended in 90% ice-cold methanol and placed on ice for 30 min.

7) The cells were centrifuged at 5000 rpm×3 min and the supernatant was removed.

8) The cells were re-suspended with 0.5% BSA (prepared with PBS), centrifuged at 5000 rpm×3 min, and washed three times.

9) 0.5-1×10$^6$ cells were aliquoted into each EP tubes. (Each kind of cells was aliquoted into 8 tubes. Among them, one tube contains blank cell and two tubes only added with second antibodies)

10) Each tube was blocked with 0.5% BSA (prepared with PBS) at room temperature for 10 min.

11) The cells were centrifuged at 5000 rpm×3 min and the block buffer was removed.

12) Each tube was added with 100 μl of primary antibody and incubated at room temperature for 30-60 min.

13) The cells were centrifuged and then the incubation buffer was removed.

14) The cells were re-suspended with 0.5% BSA (prepared with PBS), centrifuged at 5000 rpm×3 min, and washed three times.

15) The cells were added with 100 μl of FITC-labeled goat anti-mouse antibodies (for 12H23 group) or FITC-labeled donkey anti-human antibodies (for C225 group), and incubated at room temperature for 30 min 16) The cells were centrifuged and the incubation buffer was removed.

17) The cells were resuspended with 0.5% BSA (prepared with PBS), centrifuged at 5000 rpm×3 min, and washed three times.

18) The cells were resuspended with 0.5-1 ml PBS and transferred into the flow cytometry assay tube.

19) The sample of each assay tube was analyzed on flow cytometer respectively.

Results: As shown in FIG. 7A-7F, antibody 12H23 can specifically bind to cell lines expressing EGFRvIII and partially bind to A431 cells over-expressing EGFR, but hardly bind to the U87 cell lines with normally-expressed EGFR. In contrast, commercial antibody C225 (Erbitux) can bind to both cell lines with highly-expressed EGFRvIII and the U87 cell lines with normally-expressed EGFR.

The results indicated that antibody 12H23 said in the present invention had a better binding specificity.

3.2 Determination of 12H23 Affinity by the Non-Competitive Method

The wells of a 96-well microtiter plate were coated with 100 μl of 5.0 mg/L, 2.5 mg/L, 1.25 mg/L and 0.625 mg/L rEGFRvIIIex in carbonate buffer (NaHCO$_3$, pH9.6) respectively and incubated at 4° C. for 24 hours. After the coated buffer was removed, the plates were washed with PBS one time followed by adding with 350 μl of PBS containing 5% of skimmed milk powder and incubating overnight. Then the plates were washed with PBS twice. The ELISA microtiter plates containing different concentrations of solutions were added with monoclonal antibody 12H23 at an initial concentration of 1 mg/L. The obtained solution was diluted into 12 gradients by doubling dilution (diluent was PBS containing 5% of skimmed milk powder). The plates were incubated with antibodies at 37° C. for 1 hour and washed thrice with PBS. Then the plates were added with 100 μL of HRP-labeled goat anti-mouse secondary antibodies, incubated at 37° C. for 1 hour and washed 5 times with PBS followed by incubation with ABTS substrate for 15 min. The absorbance value was determined at 405 nm with a microplate reader. The binding curve was drawn according to the absorbance values to obtain the antibody concentration at half-maximal OD value (OD50%).

Results: as shown in FIG. 8, on the 5.0 mg/L coating curve, the OD50% antibody concentration is 3 μg/L ($2 \times 10^{-11}$ mol/L); on the 2.5 mg/L coating curve, the OD50% antibody concentration is 2.5 μg/L ($1.7 \times 10^{-11}$ mol/L), on the 1.25 mg/L coating curve, the OD50% antibody concentration is 2.3 μg/L ($1.5 \times 10^{-11}$ mol/L); and on the 0.625 mg/L coating curve, the OD50% antibody concentration is 2 μg/L ($1.5 \times 10^{-11}$ mol/L). The concentrations are substituted into the formula K=(n−1)/2 (nAb'−Ab) to calculate the affinity constant, wherein, Ab' and Ab represent the OD50% antibody concentration (mol/L) when the concentrations of antigen is Ag' and Ag, n=Ag/Ag'. Six K values were obtained by paired comparison and averaged to obtain the final value. The affinity constant of 12H23 is $3.8 \times 10^{10}$ L/mol and the dissociation constant Kd is $2.6 \times 10^{-11}$ mol/L.

Example 4

Binding Epitope Analysis of Monoclonal Antibody 4.1 Preparation of Recombinant Protein The S1 domain and S2 domain in EGFR extracellular region and the fusion of VK21 peptide (originated from S1 domain) with N12 domain (originated from pIII protein of M13 phage) were made respectively by conventional method (according to the method described in 1.1). The recombinant protein of EGFRvIII extracellular region was used as a positive control (FIG. 9).

Electrophoresis results indicated that the recombinant proteins rN12-S1, rN12-S2, EGFRvIIIex and rN12-VK21 were obtained (FIG. 10).

4.2 Determining the Binding Epitope of 12H23 by ELISA

The wells of a 96-well microtiter plate were coated with 100 µl of 1.0 mg/L rN12-S1, rN12-S2, EGFRvIIIex and rN12-VK21 in carbonate buffer (NaHCO$_3$, PH 9.6) respectively and incubated at 4° C. for 24 hours. After the coated buffer were removed, the plates were washed with PBS one time followed by the addition with 350 µL of PBS containing 5% of skimmed milk powder After the plates were incubated overnight, the plates were washed with PBS twice and were added with 12H23 monoclonal antibody at an initial concentration of 1 mg/L. The plates were incubated with antibodies at 37° C. for 1 hour and washed 3 times with PBS. Then the plates were added with 100 µL of HRP-labeled goat anti-mouse secondary antibodies, incubated at 37° C. for 1 hour and washed 5 times with PBS followed by incubating incubation with ABTS substrate for 15 min. The absorbance value was determined at 405 nm by a microplate reader.

Results: ELISA results were shown in FIG. 11. The antibody 12H23 can bind to EGFRvIII, rN12-S1 and rN12-VK21. The binding epitope shall be shared by these proteins, i.e. VK21 according to the structures and sequences.

```
                                          (SEQ ID NO: 11)
VK21 polypeptide sequence is VRACGADSYEMEEDGVRKCKK.
```

Example 5

The Anti-Tumor Effects of Monoclonal Antibody In Vivo 1) 3×10$^6$ Huh7-EGFRvIII tumor cells (HuH-7 liver cancer cell transfected with pLRNL, Huh-7 cell was obtained from ATCC cell bank, U.S.A) were inoculated subcutaneously into right flanks of eighteen 4-6 week old nude mice respectively.

2) Antibody C225 and antibody 12H23 were intraperitoneally administered respectively at a dosage of 0.5 mg per nude mice when the tumors had reached a mean volume of 80-100 mm$^3$ a few days later. PBS was used as a negative control. There were six mice in each group.

3) The antibodies were intraperitoneally administered three times per week for 2 weeks.

4) The tumor size was measured every other day while the mice were treated with the antibodies and the tumor size will be continually measured for 2 weeks after the final treatment. Tumor volumes were calculated using the formula: length× width$^2$/2.

5) Observation of tumor growth

Result: 12H23 could effectively inhibit the growth of Huh-EGFRvIII tumor xenografts in nude mice (As shown in FIG. 12, its inhibitory ratio was about 70% and higher than that of antibody C225).

Example 6

Determination of the Sequence of the Monoclonal Antibody

The genes with unknown 5'-flanking sequence were cloned by 5' RACE according to the following brief procedures (follow the Takara 5'-full RACE Kit instructions for the detailed operations):

1) Exposed 5' phosphate groups of total RNA were removed with Alkaline Phosphatase (CIAP). Total RNA used was 2 µg and RNA were extracted and recovered by the phenol-chloroform method.

2) A phosphate group is retained by removing 5' cap structure of mRNA with Tobacco Acid Pyrophosphatase (TAP).

3) 5' RACE Adaptor was linked to the mRNA with T4 RNA ligase and the RNA was extracted by the phenol-chloroform method.

4) Reverse transcription reaction was carried out by reverse transcriptase with the random 9-mer of deoxyribonucleotide primer provided by the Kit.

5) The reverse transcription product was used as template and target genes were amplified by the high fidelity Taq polymerase. The primers include:

```
    5': 5' RACE Outer Primer
                                          (SEQ ID NO: 12)
    (CATGGCTACATGCTGACAGCCTA)

3': heavy chain:
                                          (SEQ ID NO: 13)
    CCAGAGTTCCAGGTCACTGTCACT light chain:
                                          (SEQ ID NO: 14)
    ACACGACTGAGGCACCTCCA
```

6) The above PCR product was used as template for nested PCR. The primers include:

```
    5': 5' RACE Inner Primer
                                          (SEQ ID NO: 15)
    (CGCGGATCCACAGCCTACTGATGATCAGTCGATG)

3': heavy chain:
                                          (SEQ ID NO: 16)
    CCAGGGTCACCATGGAGTTAGTTT Light chain:
                                          (SEQ ID NO: 17)
    TGGATGGTGGGAAGATGGATACA
```

7) TA cloning and sequencing

Sequencing Result

Sequence of the heavy chain, the light chain and the CDRs of monoclonal antibody 12H23 are shown in FIG. 13-14 and the table below.

TABLE 1

Sequence of the heavy chain, light chain and the CDRs of monoclonal antibody

| Name | SEQ ID NO | Remarks |
| --- | --- | --- |
| Heavy chain (VH) coding sequence | 1 | ORF: 54-512 |
| Heavy chain (VH) amino acid sequence | 2 | |
| CDR1 | 5 | |
| CDR2 | 6 | |
| CDR3 | 7 | |
| Light chain (VH) coding sequence | 3 | ORF: 35-451 |
| Light chain (VH) amino acid sequence | 4 | |
| CDR1 | 8 | |
| CDR2 | 9 | |
| CDR3 | 10 | |

Example 7

1. Construction of the Expression Vector for Chimeric Mouse-Human Antibody Containing Coding Sequence of Antibody Variable Region Expression vector pH was constructed, which carrying hCMV promoter, cloning sites NheI and ApaI (for inserting heavy chain variable region of antibody), cloning sites, heavy chain constant region of human IgG1, internal ribosome entry site (IRES), Dihydrofolate reductase (DHFR) gene and Ampicillin resistant gene. (shown in FIG. 15A).

Expression vector pK was constructed, which carrying hCMV promoter, cloning sites EcoRV and BsiWI (for inserting light chain variable region of antibody), light chain constant region of human IgG1, internal ribosome entry site (IRES), Dihydrofolate reductase (DHFR) gene and Ampicillin resistant gene. (shown FIG. 15B).

The variable region coding sequence of heavy chain and light chain were artificially synthesized based on the light chain and heavy chain sequences identified in the example 6. NheI and ApaI restriction enzyme recognition sites were added to the two ends of the heavy chain coding sequence while the EcoRV and BsiWI restriction enzyme recognition sites were added to the two ends of the light chain coding sequence. The variable region coding sequence of heavy chain was digested with enzymes NheI and ApaI, and the variable region coding sequence of light chain was digested with enzymes EcoRV and BsiWI.

The above variable region coding sequences of heavy chain and light chain were inserted into the expression vectors (pH and pK) to construct the expression vector of anti-EGFRvIII chimeric antibody.

2. CHO Cell Transfection and Recombinant Clone Screening

*E. coli* DH5α bacteria were transformed with the above expression vector containing antibody gene, and then inoculated into 100 mL LB culture medium for amplification. The DNA purification Kit (Ultrapure Plasmid DNA Purification Kit) from Qiagen was used to extract and purify plasmid DNA. The purified plasmid DNA was used to transfect CHO cells by liposome Kit from Invitrogen, following the instruction of the manufacture.

Transfected CHO cells were consecutively cultured for 9 weeks in the MTX-selective culture medium with gradually increasing concentration, and then cultured by gradient dilution in a 96-well plate 3 times for subcloning.

Isolated monoclonal cell line was cultured in RPM1640 culture medium, and the supernatant was used for ELISA experiment. The binding strength was determined based on color reaction and these clones were confirmed to have the activity of specifically binding rEGFRvIII antigens (shown in FIG. 16). Several highly expressing clones were selected as candidate cell lines for preparing the chimeric antibody named as CH12.

Example 8

Preparation of the Conjugate

Chimeric monoclonal antibody CH12 was conjugated with diphtheria toxin (from Wuhan Institute of Biological Products Co., Ltd.) by covalent bond. Once the conjugate was added into the Huh7-EGFRvIII cells, the specific cytotoxicity can be observed. The Huh-7 cells without EGFRvIII expression can be killed only at a very high concentration of antibodies.

Example 9

Preparation of Injection

After normal saline (Sodium Chloride Injection) was added to antibody 12H23 prepared in the example 5 or chimeric antibody CH12 prepared in the example 7, and the mixture was evenly stirred and then sterilized using a 0.22 μm sterile filter. The injection was transferred as multiple aliquots into small vials (50 ml/bottle) for backup. 50 ml injection contains 50 mg of the monoclonal antibodies.

Example 10

Competitive Binding Experiment of Chimeric Antibody CH12 and Murine Monoclonal Antibody 12H23

In ELISA analysis, non-labeled CH12 antibody or 12H23 antibody at different concentrations (0, 3, 9, 27, 81, 243, 729 μg/ml) was added simultaneously with a fixed concentration (1.0 μm/ml) of HRP-labeled antibody CH12.

The results indicated that the OD405 value gradually decreases with increasing concentration of competitive antibody CH12 or 12H23. In addition the same concentration of CH12 and 12H23 have almost the same inhibiting ratio, indicating that the chimeric antibody CH12 and murine monoclonal antibody 12H23 have the similar affinity and the same binding site.

Example 11

Immunohistocytochemical Detection Using Chimeric Antibody CH12

The binding ability of chimeric antibody CH12 to Huh-7, Huh7-EGFR and Huh7-EGFRvIII was detected using the conventional immunofluorescence method.

The results indicated that antibody CH12 can significantly bind to Huh7-EGFRvIII cells and also bind to Huh7-EGFR cells which bear amplified EGFR, but hardly bind to Huh-7 cells. This indicated that the binding ability and specificity of CH12 antibody against antigen did not change after chimeric alteration.

Example 12

The Antitumor Effects of Chimeric Antibody CH12 In Vivo

1) $3 \times 10^6$ Huh7-EGFRvIII tumor cells or SMMC-7721 liver cell lines (coming from the cell bank of Academician of the Chinese Academy of Sciences) were respectively inoculated subcutaneously into right flanks of 4-6-week Balb/c nude mice. (Notes: SMMC-7721 is a liver cell line; the inventor has proved that it expresses endogenous EGFRvIII.)

2) Antibody C225, CH806 or CH12 was intraperitoneally administered respectively at a dosage of 0.5 mg per nude mice when the tumors had reached a mean volume of 150 mm$^3$ a few days later. PBS was used as a negative control. There were six mice in each group.

3) The antibodies were intraperitoneally administered three times per week for 2 weeks.

4) The tumor size was measured ever other day while the mice were treated with the indicated antibodies, and the tumor size will be continually measured for 2 weeks after the final treatment. Tumor volumes were calculated using the formula: length×width$^2$/2.

5) Observation of tumor growth.

The result showed that (FIG. 17) monoclonal antibody CH12 could effectively inhibit the growth of SMMC-7721 xenografts in vivo. The tumor inhibitory ratio is 62.94% on 25th day after the administration of antibodies (on 41th day after tumor cells inoculation), while the tumor inhibitory ratios of control antibodies (C225 and CH806) are 25.97% and 33.11% respectively.

There was significant difference between the treatment group of CH12 and control group of PBS on the 27th day after tumor cells inoculation (p<0.05). There was significant difference between the treatment group of CH12 and the treatment group of C225 on 32th day after tumor cells inoculation (p<0.05). There was significant difference between the treatment group of CH12 and the treatment group of CH806 on 37th day after tumor cells inoculation (p<0.05). These results indicated that the antitumor effect of CH12 was much better than C225 and CH806 in SMMC-7721 tumor xenografts.

In addition, CH12 can also significantly inhibit the growth of Huh7-EGFRvIII xenografts (inhibitory ratio reached 64.5%), which was better than PBS group (p=0.0001) and C225 group (inhibitory ratio is only 32.9%).

All literatures mentioned in this invention are referred in the patent, as each literature is recited as individual reference. In addition, it should be understood that technicians in the art can alter or revise the invention after referring to this invention. These equivalents shall be restricted to the claims in this invention.

REFERENCES

1) Ullrich A. et al. Human epidermal growth factor receptor cDNA sequence and aberrant expression of the amplified gene in A431 epidermoid carcinoma cells. Nature. 1984, 309: 418-425
2) Downward et al. Close similarity of epidermal growth factor receptor and v-erb B oncogene protein sequence. Nature. 1984, 307: 521-527
3) Libermann et al. Amplification, enhanced expression and possible rearrangement of EGF receptor gene in primary human brain tumors of glial origin. Nature. 1985, 313: 144-147
4) Wong et al. Increased expression of the epidermal growth factor receptor gene in malignant gliomas is invariably associated with gene amplification. Proc. Natl. Acad. Sci. USA. 1987, 84: 6899-6903
5) Yamazaki et al. Amplification of the structurally and functionally altered epidermal growth factor receptor gene (c-erbB) in human brain tumors. Molecular and Cellular Biology. 1988, 8: 1816-1820
6) Maiden et al. Selective amplification of the cytoplasmic domain of the epidermal growth factor receptor gene in glioblastoma multifome. Cancer Research. 1988 (4): 2711-2714
7) Modjtahedi H, and Dean C. The receptor for EGF and its ligands expression, prognostic value and target for therapy in cancer. International Journal of Oncology. 1994 (4): 277-296
8) Fung Y K T, et al. Activation of the cellular oncogene c-erb B by LTR insertion: molecular basis for induction of erythroblastosis by avian leukosis virus. Cell. 1983, 33:357-368
9) Yamamoto et al. A new avian erythroblastosis virus, AEV-H carries erbB gene responsible for the induction of both erythroblastosis and sarcoma. Cell. 1983, 34: 225-232
10) Nilsen et al. c-erbB activation in ALV-induced erythroblastosis: novel RNA processing and promoter insertion results in expression of an amino-truncated EGF receptor. Cell. 1985, 41: 719-726
11) Gammett et al. Differences in sequences encoding the carboxy-terminal domain of the epidermal growth factor receptor correlate with differences in the disease potential of viral erbB genes. Proc. Natl. Acad. Sci. USA. 83: 6053-6057 (1986)
12) Gilmore et al. Protein phosphorylation at tyrosine is induced by the v-erb B gene product in vivo and in vitro. Cell. 1985, 40: 609-618, (1985)
13) Kris et al. Antibodies Against a synthetic peptide as a probe for the kinase activity of the avian EGF receptor and v-erbB protein. Cell. 40:619-625 (1985)
14) Nilsen et al. c-erbB activation in ALV-induced erythroblastosis: novel RNA processing and promoter insertion results in expression of an amino-truncated EGF receptor. Cell. 1985, 41: 719-726
15) Raines et al. c-erbB activation in avian leukosis virus-induced erythroblastosis: clustered integration sites and the arrangement of provirus in the c-erbB alleles. Proc. Natl. Acad. Sci, USA. 1985, 82: 2287-2291
16) Pelley et al. Proviral-activated c-erbB is leukemogenic but not sarcomagenic: characterization of a replication-competent retrovirus containing the activated c-erbB. Journal of Virology. 1988, 62: 1840-1844
17) Wells et al. Genetic determinant of neoplastic transformation by the retroviral oncogene v-erbb. Proc. Natl. Acad. Sci. USA. 1988, 85: 7597-7601
18) Libermann et al. Amplification, enhanced expression and possible rearrangement of EGF receptor gene in primary human brain tumours of glial origin. Nature. 1985, 313: 144-147
19) Wikstrand C J, et al. Monoclonal antibodies against EGFRvIII are tumor specific and react with breast and lung carcinomas malignant gliomas. Cancer Research. 1995, 55(14): 3140-3148
20) Olapade-Olaopa E O, et al. Evidence for the differential expression of a variant EGF receptor protein in human prostate cancer. Br J Cancer. 2000, 82(1): 186-94
21) Ge H, et al. Evidence of high incidence of EGFRvIII expression and coexpression with EGFR in human invasive breast cancer by laser capture microdissection and immunohistochemical analysis. Int J cancer. 2002, 98(3): 357-61
22) Moscatello G, et al. Frequent expression of a mutant epidermal growth factor receptor in multiple human tumors. Cancer Res. 55(23): 5536-9 (1, 995)
23) Garcia de Palazzo, I E., et al. Expression of mutated epidermal growth factor receptor by non-small cell lung carcinomas. Cancer Res. 1993, 53(14): 3217-20
24) Moscatello, G. et al. Evidence for the differential expression of a variant EGF receptor protein in human prostate cancer. Br J Cancer. 2000, 82(1): 186-94
25) Luo X Y, et al. Suppression of EGFRvIII-mediated proliferation and tumorigenesis of breast cancer cells by ribozyme. Int. J. Cancer. 2003, 104(6): 716-21
26) Kuan C T, et al. EGF mutant receptor vIII as a molecular target in cancer therapy. Endocr Relat Cancer. 2001, 8(2): 83-96
27) Scott A, et al. A phase I clinical trial with monoclonal antibody ch806 targeting transitional state and mutant epidermal growth factor receptors. PNAS. 2007, 104(10): 4071-4076

The invention claimed is:

1. A $V_H$ chain of monoclonal antibody, wherein its complementarity determining region CDR comprises the following amino acid sequences of CDRs:
   CDR1 as shown in SEQ ID NO: 5,
   CDR2 as shown in SEQ ID NO: 6, and
   CDR3 as shown in SEQ ID NO: 7.

2. The $V_H$ chain of monoclonal antibody of claim 1, wherein the amino acid sequence is as set out in SEQ ID NO: 2.

3. A $V_L$ chain of monoclonal antibody, wherein its complementarity determining region CDR comprises the following amino acid sequences of CDRs:
   CDR1 as shown in SEQ ID NO: 8,
   CDR2 as shown in SEQ ID NO: 9, and
   CDR3 as shown in SEQ ID NO: 10.

4. The $V_L$ chain of monoclonal antibody of claim 3, wherein the amino acid sequence is as set out in SEQ ID NO: 4.

5. A monoclonal antibody or its conjugate, wherein the amino acid sequences of its $V_H$ chain is as set out in SEQ ID NO: 2, and the amino acid sequences of its $V_L$ chain is as set out in SEQ ID NO: 4.

6. The monoclonal antibody of claim 5, wherein the said antibody is murine antibody, humanized antibody, or chimeric antibody.

7. A DNA molecule, wherein it encodes the following protein selected from: a $V_H$ chain of a monoclonal antibody, wherein its complementarity determining region CDR comprises the following amino acid sequences of CDRs:
   CDR1 as shown in SEQ ID NO: 5,
   CDR2 as shown in SEQ ID NO: 6, and
   CDR3 as shown in SEQ ID NO: 7;
   a $V_L$ chain of a monoclonal antibody, wherein its complementarity determining region CDR selected from the following amino acid sequences of CDRs:
   CDR1 as shown in SEQ ID NO: 8,
   CDR2 as shown in SEQ ID NO: 9, and
   CDR3 as shown in SEQ ID NO: 10;
   a monoclonal antibody, wherein the amino acid sequences of its $V_H$ chain is as set out in SEQ ID NO: 2, and the amino acid sequences of its $V_L$ chain is as set out in SEQ ID NO: 4.

8. The DNA molecule of claim 7, wherein it has the following DNA sequence selected from SEQ ID NO: 1, 3.

9. A pharmaceutical composition, wherein it comprises a monoclonal antibody and a pharmaceutically acceptable carrier, the $V_H$ chain of the said monoclonal antibody comprises the complementarity determining regions of SEQ ID NOs: 5-7 and the $V_L$ chain of the said monoclonal antibody comprises the complementarity determining regions of SEQ ID NO:8-10;
   or, the $V_H$ chain of the said monoclonal antibody comprises the amino acid sequence of SEQ ID NO:2, and the VL chain of the said monoclonal antibody comprises the amino acid sequence of SEQ ID NO:4.

* * * * *